(12) United States Patent
Westman et al.

(10) Patent No.: US 7,378,240 B2
(45) Date of Patent: May 27, 2008

(54) SYNTHESIS AND EVALUATION OF NEW CYANINE DYES AS MINOR GROOVE OF [POLY(DA-DT)]$_2$ BINDERS

(75) Inventors: Gunnar Westman, Härryda (SE); Jonas Karlsson, Göteborg (SE)

(73) Assignee: Light Up Technologies AB, Huddinge (SE)

( * ) Notice: Subject to any disclaimer, the term of this patent is extended or adjusted under 35 U.S.C. 154(b) by 350 days.

(21) Appl. No.: 10/605,961

(22) Filed: Nov. 10, 2003

(65) Prior Publication Data

US 2004/0132046 A1  Jul. 8, 2004

Related U.S. Application Data

(63) Continuation of application No. PCT/SE02/00860, filed on May 10, 2002.

(30) Foreign Application Priority Data

May 10, 2001 (SE) .................... 0101651

(51) Int. Cl.
- *C12Q 1/68* (2006.01)
- *C07D 401/14* (2006.01)
- *C07D 413/14* (2006.01)
- *C07D 417/14* (2006.01)

(52) U.S. Cl. ...................... 435/6; 546/152; 546/270.1; 546/271.7; 546/273.4

(58) Field of Classification Search ................ 546/152, 546/270.1, 271.7, 273.4, 167, 176; 435/6
See application file for complete search history.

(56) References Cited

U.S. PATENT DOCUMENTS 5,656,449 A   8/1997  Yue

FOREIGN PATENT DOCUMENTS

WO    WO 01/94473 A1    12/2001
WO    WO 02/090443 A1    11/2002

OTHER PUBLICATIONS

Carlsson et al., Optical and photophysical properties of the oxazole yellow DNA probes YO and YOYO, J. Phys. Chem., 1994, pp. 10313-10321, vol. 98.
Colson et al., Electric linear dichroism as a new tool to study sequence preference in drug binding to DNA, Biophysical Chemistry, 1996, pp. 125-140, vol. 58.
Deligeorgiev et al., Preparation of Intercalating Dye Thiazole Orange and Derivatives, Dyes and Pigments, 1995, pp. 315-322, vol. 29, No. 4.
Gurrieri et al., Direct Visualization of individual DNA Molecules by Fluorescence Microscopy: Characterization of the Factors Affecting Signal/Background and Optimization of Imaging Conditions Using YOYO, Analytical Biochemistry, 1997, pp. 44-53, vol. 249.
Haugland, Nucleic Acid Stains, Handbook of Fluorescent Probes and Research Chemicals, 1996, pp. 144-152, 6th Edition, No. 8.
Isacsson et al., Solid-phase synthesis of asymmetric cyanine dyes, Tetrahedron Letters, 2001, pp. 3207-3210, vol. 42.
Jorgenson et al., Interaction of Hoechst 33258 with Repeating Synthetic DNA Polymers and Natural DNA, Journal of Biomolecular Structure & Dynamics, 1988, pp. 1005-1023, vol. 5, No. 5.
Kapuscinski et al., Fluorescent complexes of DNA with DAPI 4'6-diamidine-2-phenyl indole.2HCI or DCI 4',6-dicarboxyamide-2-phenyl indole, Nucleic Acids Res., 1978, pp. 3775-3799, vol. 5, No. 10.
Kubista et al., Characterization of Interaction between DNA and 4',6-Diamidino-2-phenylindole by Optical Spectroscopy, Biochemistry, 1987, pp. 4545-4553, vol. 26.
Larsson et al., Characterization of the Binding of YO to [Poly(dA-dT)]$_2$ and [Poly (dG-dC)]$_2$ and of the Fluorescent Properties of YO and YOYO Complexed with the Polynucleotides and Double-Stranded DNA, Biopolymers, 1995, pp. 153-167, vol. 36.
Larsson et al., Characterization of the Binding of the Fluorescent Dyes YO and YOYO to DNA by Polarized Light Spectroscopy, 1994, pp. 8459-8465, vol. 116.
Lee et al., Thiazole Orange: A New Dye for Reticulocyte Analysis, Cytometry, 1986, pp. 508-517, vol. 7.
Lyng et al., The CD of Ligand—DNA Systems. 2. Poly (dA-dt) B-DNA, Biopolymers, 1992, pp. 1201-1214, vol. 32.
Matsuzawa et al., Change of the Higher Order Structure in a Giant DNA Induced by 4', 6-Diamidino-2-Phenylindole as a Minor Groove Binder and Ethidium Bromide as an Intercalator, Nucleosides & Nucleotides, 1994, pp. 1415-1423, vol. 13, No. 6 & 7.
Mikheikin et al., Binding of Symmetrical Cyanine Dyes into the DNA Minor Groove, Journal of Biomolecular Structure & Dynamics, 2000, pp. 59-72, vol. 18, No. 1.
Mital et al., Synthesis of Some 5-Substituted 2-Aminobenzenethiols and their Conversion into Phenothiazines via Smile Rearrangement, J. Chem. Soc., 1969, pp. 2148-2150.
Naim et al., Studies in antiparasitic agents: Part 17—Synthesis of 2-acylamino-6-substituted-benzthiazoles as potential anthelmintic agents, Indian Journal of Chemisty, 1991, pp. 494-498, vol. 30B.
Neidle, Crystallographic Insights into DNA Minor Groove Recognition by Drugs, Biopolymers, 1997, pp. 105-121, vol. 44.
Netzel et al., Base-Content Dependence of Emission Enhancements, Quantum Yields, and Lifetimes for Cyanine Dyes Bound to Double-Strand DNA: Photophysical Properties of Monomeric and Bichromophoric DNA Stains, J. Phys. Chem., 1995, pp. 17936-17947, vol. 99.
Norden et al., Linear dichroism spectroscopy of nucleic acids, Quarterly Review of Biophysics, 1992, pp. 51-170, vol. 25, No. 1.
Nygren et al., The Interactions Between the Fluorescent Dye Thiazole Orange and DNA, Biopolymers, 1998, pp. 39-51, vol. 46.

(Continued)

*Primary Examiner*—Bernard Dentz
(74) *Attorney, Agent, or Firm*—Birch, Stewart, Kolasch & Birch, LLP

(57) ABSTRACT

The present invention relates to new cyanine dyes according to the formula (I), wherein $A_1$ and $A_2$ are each independently O, S, or N, and R is H or a carbohydrate that may contain a hetero atom, and m is 0 to 5, and n is 0 to 5.

20 Claims, 15 Drawing Sheets

OTHER PUBLICATIONS

Ogul'Chansky et al., Interactions of cyanine dyes with nucleic acids. XXIV. Aggregation of monomethine cyanine dyes in presence of DNA and its manifestation in absorption and fluorescence spectra, Spectrochimica Acta—Part A, 2001, pp. 1525-1532, vol. 57.

Petty et al., Thermodynamic Characterization of the Association of Cyanine Dyes with DNA, J. Phys. Chem. B, 2000, pp. 7221-7227, vol. 104.

Rye et al., Stable fluorescent complexes of double-stranded DNA with bis-intercalating asymmetric cyanine dyes: properties and applications, Nucleic Acids Res., 1992, pp. 2803-2812, vol. 20, No. 11.

Seifert et al., Spontaneous Assembly of Helical Cyanine Dye Aggregates on DNA Nanotemplates, J. Am. Chem. Soc., 1999, pp. 2987-2995, vol. 121.

Singer et al., Characterization of PicoGreen Reagent and Development of a Fluorescence-Based Solution Assay for Double-Stranded DNA Quantitation, Analytical Biochemistry, 1997, pp. 228-238, vol. 249.

Svanvik et al., Light-Up Probes: Thiazole Orange-Conjugated Peptide Nucleic Acid for Detection of Target Nucleic Acid in Homogeneous Solution, Analytical Biochemistry, 2000, pp. 26-35, vol. 281.

Wilson et al., Binding of 4',6-Diamidino-2-phenylindole (DAPI) to GC and Mixed Sequences in DNA: Intercalation of a Classical Groove-Binding Molecule, J. Am. Chem. Soc., 1989, pp. 5008-5010, vol. 111.

Yoshinaga et al., Intercalating Fluorescence Dye YOYO-1 Prevents the Folding Transition in Giant Duplex DNA, Biochemical and Biophysical Research Communications, 2001, pp. 264-267, vol. 286.

Zhou et al., Blue Sensitizing Dyes: Synthesis, Spectroscopy, and Performance in Photographic Emulsions, Journal of Imaging Science and Technology, 1995, pp. 244-252, vol. 39, No. 3.

Zubarovskii et al., Asymmetric imidacarbocyanines with hetaryls as substituents, Chemical Abstracts, 1975, pp. 851-854, vol. 41, No. 8.

Prenna et al., "Automated determination of DNA cellular content (Feulgen) improved by using BBT-$SO_2$ in flow cytofluorometry," Pulse-Cytophotometry, 1976, pp. 88-95.

Latt et al., "New Fluorochromes, Compatible with High Wavelength Excitation, for Flow Cytometric Analysis of Cellular Nucleic Acids," Cytometry, vol. 5, No. 4, pp. 339-347, Jul. 1984.

Singh et al., "Synthetic Utility of Catalytic Fe(III)/Fe(II) Redox Cycling Towards Fused Heterocycles: A Facile Access to Substituted Benzimidazole, Bis-benzimidazole and Imidazopyridine Derivatives," Synthesis, 2000, No. 10, pp. 1380-1390.

| Dye | X | Heterocycle | λ$_{max}$ |
|-----|---|-------------|-----------|
| BO  | S | pyridine    | 445       |
| TO  | S | quinoline   | 510       |
| PO  | O | pyridine    | 435       |
| YO  | O | quinoline   | 480       |

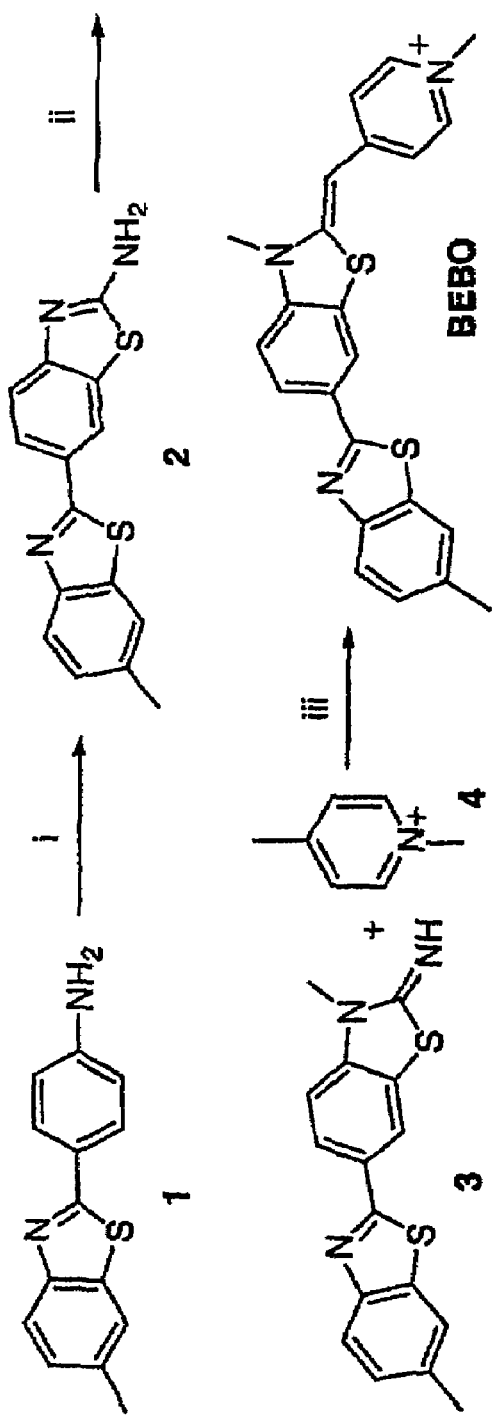
Scheme 1
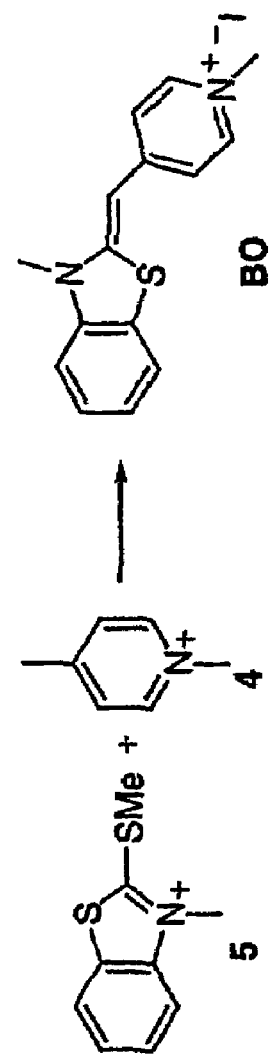
Scheme 2

SYNTHESIS AND EVALUATION OF NEW CYANINE DYES AS MINOR GROOVE OF [POLY(DA-DT)]₂ BINDERS

DESCRIPTION

1. Technical Field

The present invention relates to new cyanine dyes particularly suited for use in DNA sequencing in particular minor groove [poly(dA-dT)]$_2$ binders.

2. Background of the Invention

The introduction of combinatorial chemistry, the sequencing of the human genome and miniaturisation, e.g. lab-on a chip, nanochemistry, has enabled the creation of vast libraries of "new chemical entities", millions of which must be quickly tested by high-throughput screening to identify active sites and drugs. Drugs that bind reversibly to DNA in the minor groove of DNA have been synthesised with the aim to generate new lead compounds with anticancer and antiviral properties. Formerly, radioactive probes have been used to study the effects of drug-DNA interactions but during the last years they have started to be replaced by different fluorogenic assays. Today, drug-DNA interactions are mainly studied with absorbance spectroscopy, fluorescence dye displacement assays, footprinting or NMR. Since the numbers of fluorescence markers are limited to a few there is a challenge to discover new fluorescent dyes that circumvent the limitations on those that now are available. New fluorogenic compounds that bind in the minor groove can either work in dye displacement assays or give insight in how substituents may work as minor groove recognition elements.

Fluorogenic compounds can provide tremendous sensitivity due to their large quantum emission yield upon excitation. A limitation is that there are not many fluorophores that give a high increase in fluorescence upon hybridisation or reaction with targets.

Asymmetric cyanine dyes have achieved much interest due to their excellent nucleic acid staining properties. Upon binding to nucleic acids such dyes usually exhibit a large enhancement in fluorescence intensity[1] and are widely used as fluorescent markers for DNA in various contexts.[2-4] The interaction between double stranded DNA and the asymmetric cyanine dyes TO and YO (FIG. 1) have been investigated spectroscopically in several studies and were found to bind by intercalation[5-7] in a non-specific fashion.[8] They also bind strongly to single stranded DNA with a large accompanying increase in fluorescence intensity.[9] This makes the dyes less useful in studies where only a signal from double stranded DNA is desirable. There are, however, fluorescent ligands that bind in the minor groove instead of by intercalation that bind selectively to double and not to single stranded DNA, e.g. DAPI[10] and Hoechst-derivatives.[11] In contrast to most cyanine dyes these ligands have a DNA sequence selectivity, preferably for A/T-rich segments.[12] Furthermore, compared to the intercalating dyes they exert a smaller perturbation of the DNA-duplex upon binding. This is valuable in studies where its critical that the DNA is not stretched out, for example in certain fluorescence microscopy studies.[13,14] Minor groove binders do not, however, exhibit an equally dramatic increase in fluorescence as the asymmetric cyanine dyes upon binding to DNA, which can display more than a thousand-fold increase.[1] For BO (FIG. 1) a 400-fold enhancement in fluorescence has been reported,[15] whereas Hoechst and DAPI exhibit a ~95-fold[16] and a ~20-fold[17] increase, respectively. Another advantage of the asymmetric cyanine dyes as labels for DNA is their relatively long absorption maxima, which reduces problems of background absorption from biological material. The absorption maxima of the dyes in FIG. 1 when bound to DNA varies from roughly 435 nm to 510 nm[6,9,17] compared to around 350 nm for Hoechst 33258 (Hoechst) and DAPI.[17] A dye that combines the features of the minor groove binding ligands and the photophysical properties of the ordinary asymmetric cyanine dyes would thus be of great value for detection and studies of DNA.

As an initial effort towards such a dye we designed the asymmetric cyanine dye BEBO (Scheme 1). This dye has the same cyanine chromophore as the intercalating dye BO but the structure is extended with a benzothiazole substituent in the 6-position. The positioning of the benzothiazole moiety gives BEBO a crescent-shape similar to that of other minor groove binders, e.g. Hoechst. The short synthetic route to BEBO starting from the commercially available benzothiazole substituted aniline 1 motivated the choice of the benzothiazole group (Scheme 1). In addition, symmetrical cyanine dyes containing two benzothiazole moieties have been suggested to bind in the minor groove either as monomers[18] or as dimers.[19] Herein we describe the synthesis and DNA binding studies of BEBO and the analogous dye BO.

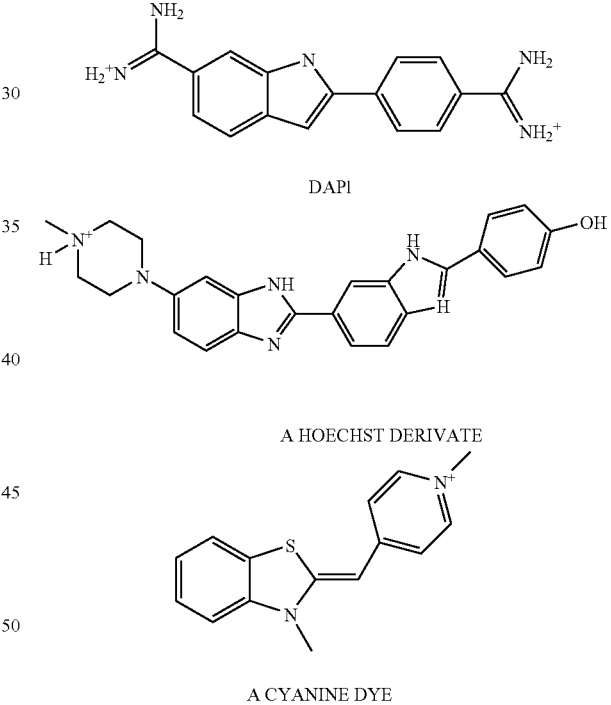

The fluorophores that are most frequently used today are Fluorescein, BODIPY, DAPI, Hoechst and asymmetric cyanine dyes such as TO, YO and TOTO. Fluorescein and BODIPY are the most common fluorescent reporter groups for covalent labeling of proteins whereas DAPI, Hoechst and Cyanine dyes are the most common fluorophores for detection of nucleic acid.

DAPI (abs. max 400 nm) and Hoechst (abs. max 350 nm) bind in the minor groove and are used as base-specific fluorescent probes for DNA with a 20-fold increase in fluorescence upon binding to DNA. In contrast, asymmetric cyanine dyes has shown up to a 18,000-fold increase in fluorescence upon binding to DNA. They also have the advantage that the absorption and emission can be easily varied by changing the number of double bounds between the aromatic rings. However, a major drawback with asymmetric cyanine dyes is that they usually bind in a non-specific fashion towards DNA-sequences. (i.e. intercalate or form ion-pair complexes to DNA which may result in complex or weak fluorescence signal.) Therefore a cyanine dye that bind in a more organised way may have high fluorescence increase upon hybridisation and thus, be a more sensitive fluorophores.

The minor groove is a convenient site for attack since it is normally unoccupied by cellular compounds such as proteins. It is also a perfect complement to concave cationic dyes due to the negative electrostatic potential and the convex floor of the minor groove. Certain minor groove binders stabilise DNA duplexes and can work as regulators of DNA-protein function. As a consequence, the development of sequence-specific minor groove binders may generate new compounds with anticancer and/or antiviral properties and thus, serve as an alternative and complementary approach to the antisense oligonucleotide strategy. Furthermore, the minor groove binder's stabilising effect upon DNA duplexes can be used in probes, consisting of a minor-groove ligand-nucleic acid conjugate, to increase the melting temperatures (Tm) of probe-DNA duplexes. An increase of the Tm of probes will allow a more flexible assay design since the oligo in the probe can be shorter and still have an optimal Tm.

Sequence selective minor groove binders also has mismatch discrimination. Nucleic acid probes with minor groove binders as a reporter group should have an increased difference between the Tm of matched and single-base mismatched nucleic acids than the corresponding probe with an intercalator as a reporter group. Thereby increasing the discriminatory power of hybridisation assays.

A useful feature of minor groove binders are a preference for double stranded DNA compared to single stranded DNA whereas intercalators usually has no preference for single or double stranded DNA. This feature results in minor groove binder probes which have lower background fluorescence than probes with an intercalator and as a consequence, a greater signal-to-noise ratio upon hybridisation. Furthermore, dyes specific for duplex-DNA can be used for quantification of DNA in mixtures contaminated by RNA or single stranded DNA.

SUMMARY OF THE PRESENT INVENTION

One challenge is to develop numbers of highly sensitive fluorescent dyes with different well-separated emission spectra that bind in a precise way and thus allow multidetection of a series of targets with high sensitivity. As mentioned, cyanine dyes can have up to a 18,000-fold increase in fluorescence upon hybridisation which is almost 1000 times higher than the minor groove binders that are used today. Also the absorption and emission are easily turned by varying the conjugated system in cyanine dyes. Thus, a cyanine dye substituted so that binding in the minor groove is governed but with the extraordinary fluorescence properties of the known cyanine dyes retained seems to be a highly interesting target compound.

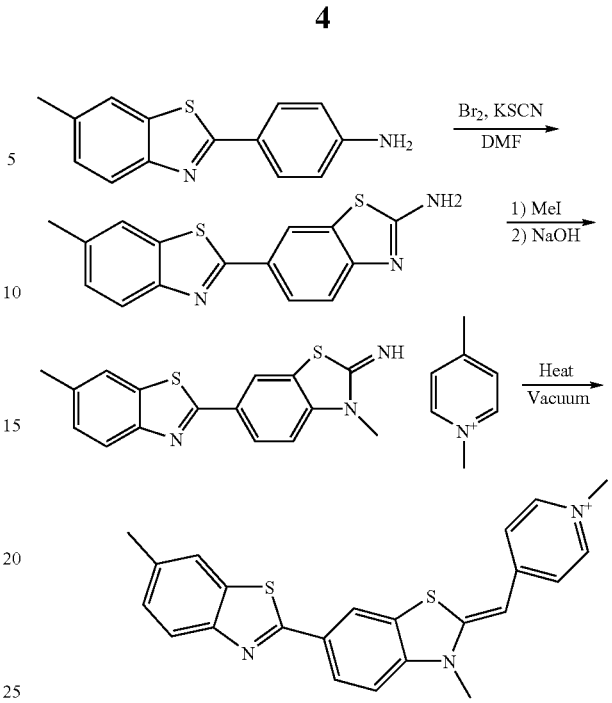

Inspired by the concave structure of minor groove binders and the new findings that a benzothiazole and groups having a related structure may govern minor groove recognition, an asymmetric cyanine dye substituted with an extra benzothiazole group has been synthesized in accordance with the above.

The interaction between this new dye and DNA were studied with various spectroscopic methods such as flow-LD and CD.

These two techniques can provide information on whether a drug is binding to DNA by intercalation or groove binding. Weak induction of CD is usually associated with intercalating whereas asymmetric induction is due to groove binding. Groove binding gives a strong signal in Flow-LD.

In the presence of calf thymus DNA a weak positive signal was observed in the flow LD-spectra. This can be due to heterogeneous binding with a mixture of intercalated and groove binding dye. On the other hand, in the presence of poly [(dA-dT)]$_2$ a clear positive LD is shown providing a strong indication of minor groove binding. For poly [(dG-dC)]$_2$ only a weak negative signal was observed indicating a heterogeneous binding or a low abundance of intercalated dye.

Figure 1:
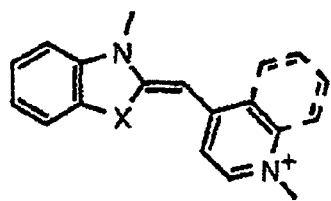
FIG. 1. Intercalating asymmetric cyanine dyes.

Scheme 1. Reagents and conditions: I, Br$_2$, KSCN, DMF, 3 h; ii, 1. MeI, DMSO, 17 h, 110° C., 2. NaOH$_{aq}$, DMSO; iii, 160° C., vacuum 1 h.

Scheme 2. Reagents and conditions: Triethylamine, dichloromethane, rt 14 h.

DETAILED DESCRIPTION OF THE PRESENT INVENTION

It has now turned out that the following compounds solve the above discussed problems and the invention is mainly characterized by new compounds according to the following: A cyanine dye binding in the groove of DNA, selected from the group of:

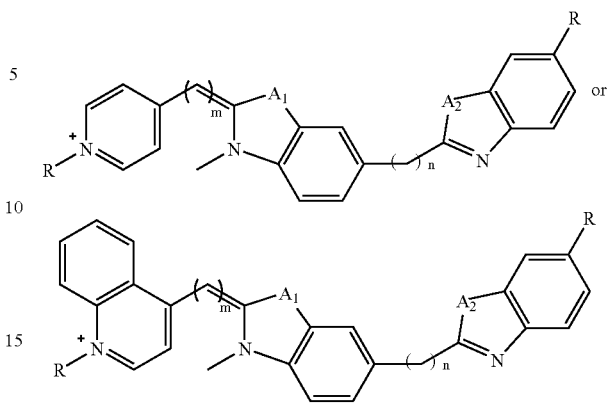

wherein $A_1$ and $A_2$ are each independently O, S, or N, and R is H or a carbohydrate that may contain a hetero atom, and m is 0 to 5, and n is 0 to 5.

In one embodiment the cyanine dye has R being methyl, or ethyl, and m being 1 and n being 0.

In one embodiment the cyanine dye has R being methyl, or ethyl, and m being 1 and n being 0 and $A_1$ and $A_2$ being S.

In one embodiment the cyanine dye has R being methyl, or ethyl, and m being 1 and n being 0 and $A_1$ and $A_2$ being O.

In one embodiment cyanine dye has R being methyl, or ethyl, and m being 1 and n being 0 and $A_1$ being S and $A_2$ being O.

In one embodiment the cyanine dye has the pyridine/quinoline ring in the 2-position.

One aspect of the present invention provides a probe for nucleic acid hybridization comprising a cyanine dye according to the above.

A further aspect of the present invention provides a method for carrying out a real-time PCR-reaction of a DNA template, wherein a fluorescent dye increases its fluorescent reaction when it is bound in a minor groove position in a double stranded DNA, whereby the dye comprises at least 2 aromatic ring systems both comprising at least one nitrogen atom, which rings are linked by an alkine group having up to four carbon atoms to form a conjugated bond, and the dye further comprises at least a third aromatic system linked thereto via a bond having a significant double string character, such as a single bond or a ethyne bond, to provide a stiff conjugated system.

In one embodiment of the method the dye is an asymmetric cyanine dye.

In one embodiment of the method, one of the cyanine residues contains S and/or O.

In one embodiment of the method the dye compound is crescent shaped.

In one embodiment the dye is a derivative according to the general formulas given above.

Clearly the new dye binds differently to A-T rich and G-C rich regions. Results from CD-measurements gave further support for groove binding of this new dye.

For poly GC almost no signal is seen which is consistent with intercalative or external binding, whereas for poly AT a very strong asymmetric induction is seen.

It binds to the minor groove of A-T rich regions and thus it stabilises A-T bonds more than G-C bonds in a DNA duplex. Therefore, if a probe is designed so that an A-T rich region is placed under the minor groove binder it can be used in probes to improve mismatch discrimination.

Interestingly, our results further accentuate the preliminary reports in the literature that the benzothiazole group has utility as a minor groove recognition element. If so, this is an important finding, since it opens possibilities for design of new drugs binding in the minor groove.

Our first results show that it is possible to design and prepare asymmetric cyanine dyes that work as minor groove binders.

Further, possibilities of broadening the present scope are: Since there is a well working synthetic route for the substituted cyanine dye the first step is the nitrogen in ortho position, 2-BEBO, from the methine substituent.

Along with the synthesis of the two quinolinium derivatives, BETO and 2-BETO, the synthesis of the benzoxazole and benzimidazole derivatives can be done.

The synthesis of these new benzoxazole and benzimidazole substituted dyes will follow a slightly different synthetic route.

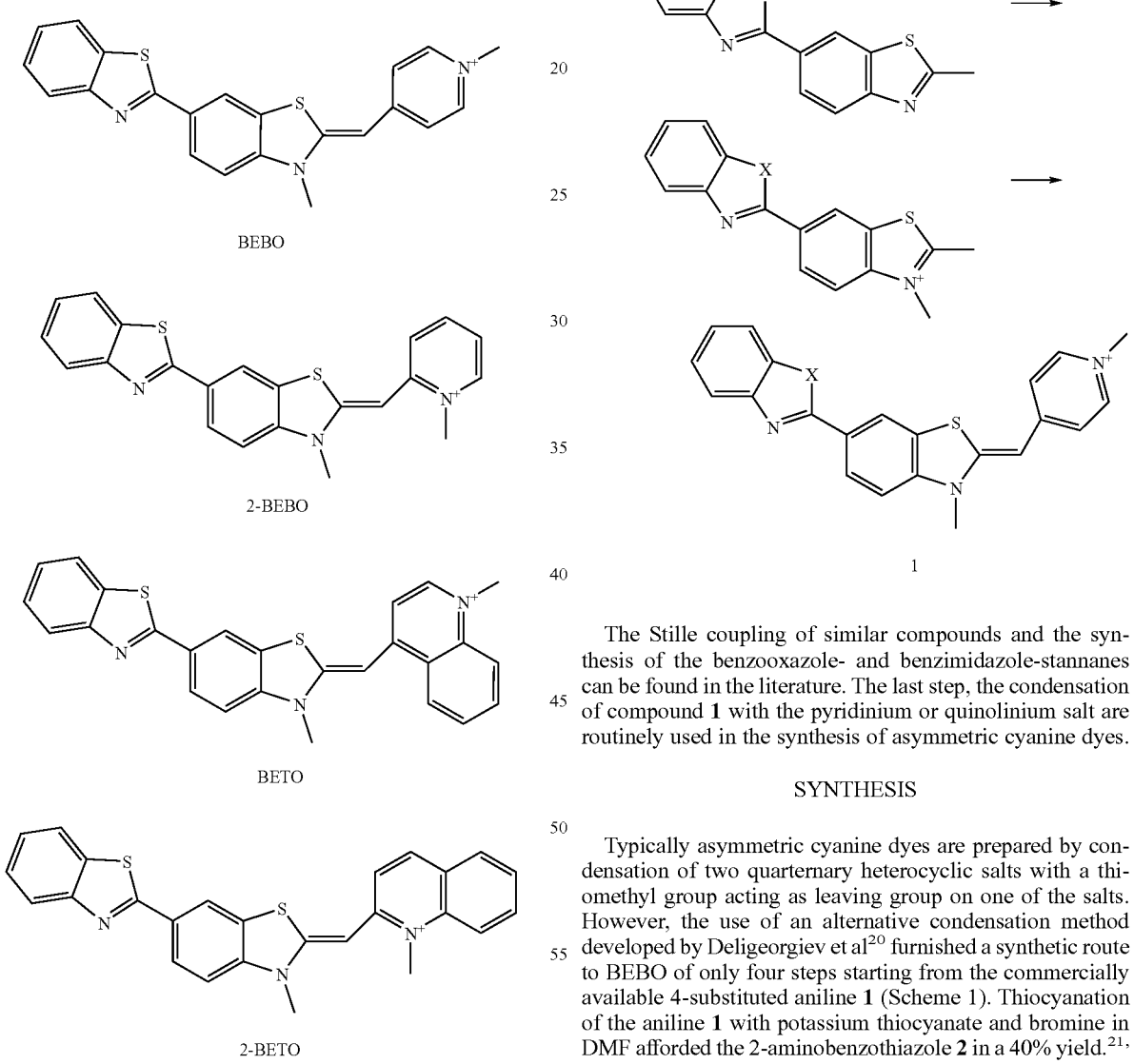

The Stille coupling of similar compounds and the synthesis of the benzooxazole- and benzimidazole-stannanes can be found in the literature. The last step, the condensation of compound 1 with the pyridinium or quinolinium salt are routinely used in the synthesis of asymmetric cyanine dyes.

SYNTHESIS

Typically asymmetric cyanine dyes are prepared by condensation of two quarternary heterocyclic salts with a thiomethyl group acting as leaving group on one of the salts. However, the use of an alternative condensation method developed by Deligeorgiev et al[20] furnished a synthetic route to BEBO of only four steps starting from the commercially available 4-substituted aniline 1 (Scheme 1). Thiocyanation of the aniline 1 with potassium thiocyanate and bromine in DMF afforded the 2-aminobenzothiazole 2 in a 40% yield.[21, 22] Methylation of 2 by iodomethane and subsequent deprotonation proceeded in a total 77% yield to produce the 2-imino-3-methyl-benzothiazoline 3. The dye BEBO was prepared in 24% by simply melting the benzothiazoline 3 together with the pyridinium salt 4 at 160° C. under vacuum.[20]

To enable comparative DNA binding studies the presumed intercalating dye BO (1-methyl-4-[(3-methyl-2(3H)- benzothiazolylidene)methyl]-pyridinium iodide) was synthesised according to the classical method using a modified procedure by Zhou et al (Scheme 2).[23] The dye was afforded in 46% yield by condensation of the pyridinium salt 4 and the benzothiazolium salt 5 in dichloromethane using triethyl amine as base.

LINEAR DICHROISM MEASUREMENTS

Figure 2:
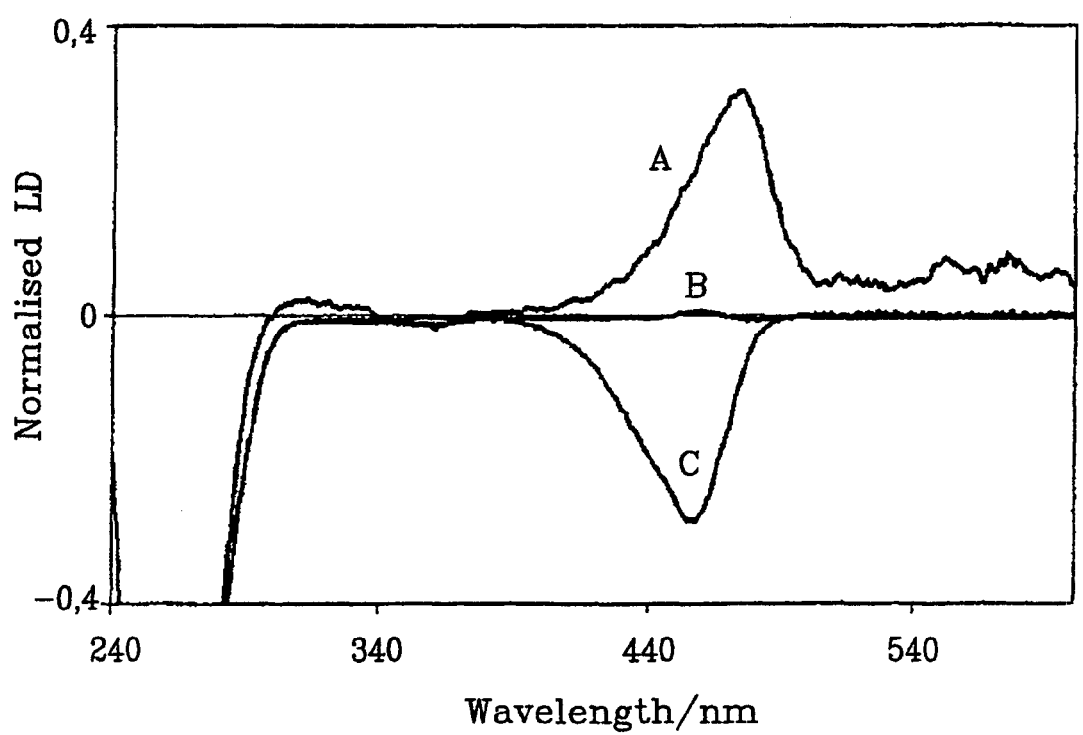
FIG. 2. Flow LD spectra of BEBO complexed with: A) [poly(dA-dT)]$_2$, B) ctDNA and C) BO complexed with ctDNA, normalised at the DNA base transition. Binding ratio R, dye:bases, were 0.05. [dye]=11 µM in all spectra.

To study the effect induced by the benzothiazole substituent in BEBO on its interaction with DNA, binding studies of the analogous dye BO were also performed as a comparison. FIG. 2 shows the flow linear dichroism (LD) spectra of BEBO and BO with different DNA. LD is defined as the difference in absorption of light polarized parallel and perpendicular to the macroscopic axis of orientation. The LD-spectra of oriented DNA-ligand complexes may be analysed in terms of angles that the electronic transition moments of the ligands make with the DNA-helix axis to provide information about binding geometries.[24] The orientation of the DNA complexes was achieved using a flow Couette cell with outer rotating cylinder. For BEBO in the presence of [poly (dA-dT)]$_2$ (poly-AT) a clear positive LD is shown providing a strong indication of minor groove binding (FIG. 2). From the reduced LD, obtained through division of the LD by the isotropic absorption, the angle between the long wavelength transition moment of BEBO and the DNA-helix was calculated to be 44°. This is very similar to the angle for known minor groove binders, e.g., DAPI.[25] The major transition moment of BEBO can be expected to be polarized roughly along the line connecting the pyridine with the closest benzothiazole ring.[26] The weaker positive signal shown for BEBO in the presence of calf thymus DNA (ctDNA) is possibly due to binding in the minor groove with an angle close to 54°, as suggested in earlier studies of symmetrical cyanine dyes.[13] However, the binding-angle to poly-AT of 44° in addition with CD-titration data (see below) proposes a more complicated binding to ctDNA with a mixture of binding modes resulting in an average low LD signal. Although Hoechst and DAPI have a preference for minor groove binding to AT-rich regions it has been suggested that they bind to GC sequences by a non-classical intercalation process.[27,28] This model seems to be applicable here also, since the reduced LD spectrum of BEBO with [poly(dG-dC)]$_2$ (poly-GC) show a negative value of the same amplitude as for the DNA bases indicating intercalation (data not shown).

Figure 3:
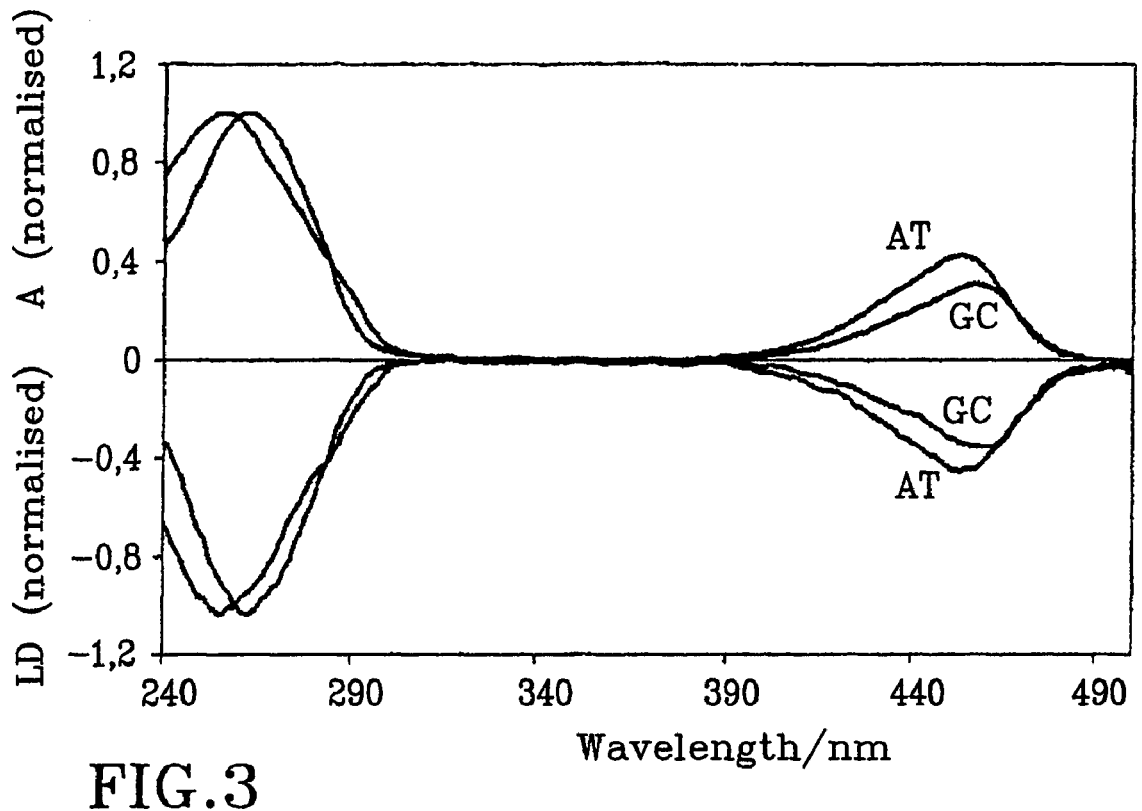
FIG. 3. Normalised LD and absorption spectra of BO in presence of: AT) [poly (dA-dT)]$_2$, GC) [poly (dG-dC)]$_2$, [BO]=11 µM. R=0.025.

In contrast to the binding of BEBO, LD measurements indicate that BO binds by intercalation to all three different polynucleotides studied: ctDNA (FIG. 2), poly-AT and poly-GC (FIG. 3). The change in binding mode induced by the benzothiazole extension of the BO structure is particularly apparent in the case of poly-AT.

CIRCULAR DICHROISM MEASUREMENTS

Figure 4A:
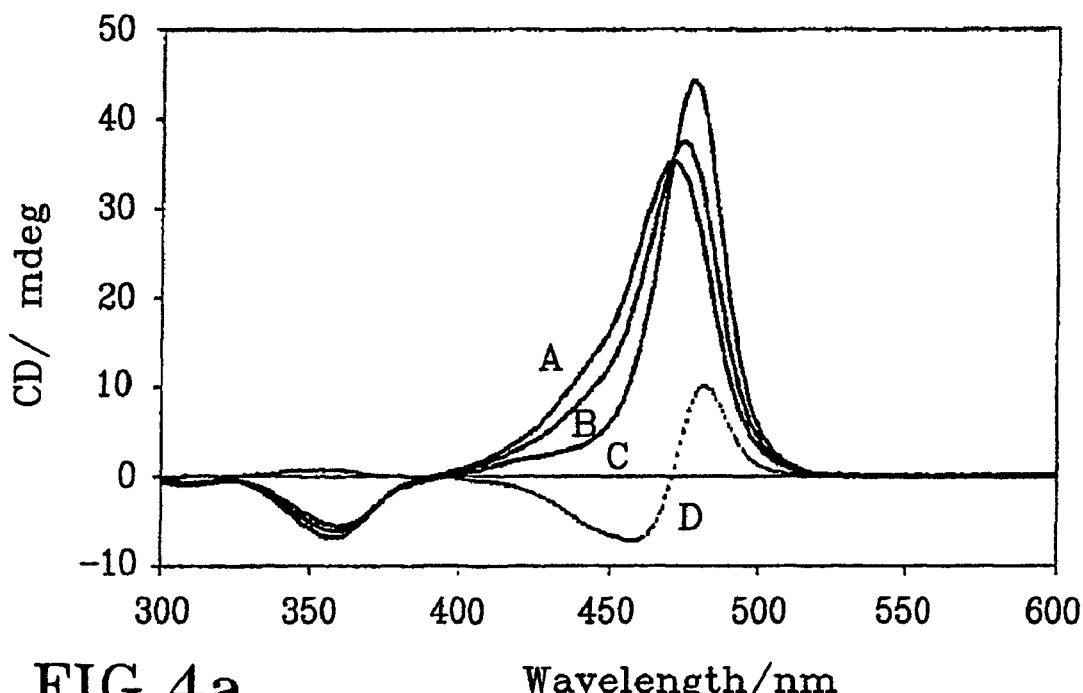
FIG. 4a-b. CD spectra of BEBO in presence of (a) [poly (dA-dT)]$_2$, [R=0.025 (A), 0.05 (B), 0.10 (C), (D)=(C)−(B)] and (b) ctDNA (R values from bottom to top are 0.1, 0.05, 0.033, 0.025 and 0.0125). [dye]=11 µM in all spectra.

The strongly induced positive CD for BEBO in presence of poly-AT (FIG. 4a) gives further strong support for binding in the minor groove.[29] FIG. 4a shows the titration of poly-AT into BEBO with binding ratios R, defined as the total number of dye molecules per base, varying from 0.025 to 0.1. The larger CD amplitude of BEBO at the highest binding ratio is rationalized by a contribution of exciton coupling interactions between closely bound chromophores. This is illustrated by subtracting the B spectrum (R=0.05) from the C spectrum (R=0.1) in FIG. 4a to produce a spectrum typical of exciton coupling (D, FIG. 4a).

Figure 4B:
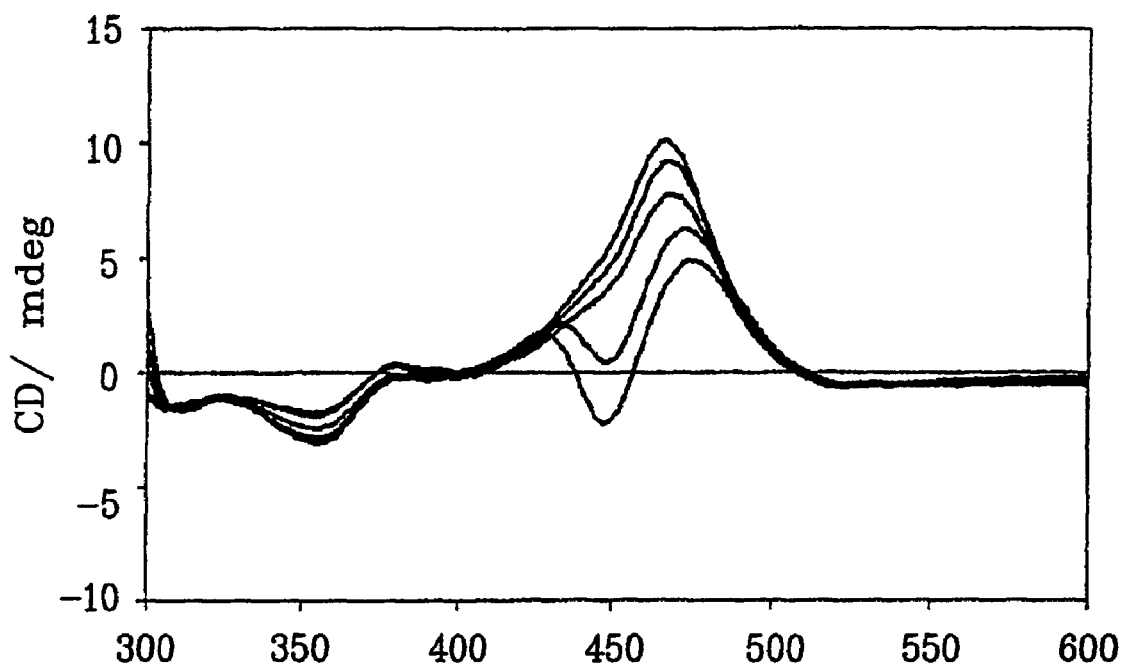

In the presence of ctDNA, the induced CD is smaller but still, intercalation or external stacking of the dye would not give rise to this large amplitude. Thus, there must be a significant amount of dye residing in the minor groove. The titration of ctDNA into BEBO with binding ratios R varying from 0.0125 to 0.10 is shown in FIG. 4b. As with the binding of BEBO to poly-AT, there is feature of exciton coupling interactions between closely spaced ligands at higher binding ratios. At lower binding ratio the signal is similar to that of the corresponding poly-AT spectra, albeit with smaller amplitude.

The binding of BEBO to poly-GC gave rise to only a very small induced CD (FIG. 5a), which supports an intercalative binding mode to GC-regions. This might partly account for the lower CD obtained upon binding to ctDNA. However, one must bear in mind that ctDNA is more complex than just a mixture of alternating GC- and AT-segments. The amplitude of the CD spectra in the presence of ctDNA is about one fourth of the poly-At spectra. If the binding to ctDNA is a mixture of groove binding to AT-regions and intercalation to GC-regions then 75 percent would be bound in an intercalative fashion. This does not hold since the LD should be significantly more negative in that case. Hence, a substantial amount of dye must be bound in a non-intercalative fashion to ctDNA at sites affording a lower induced CD than when bound to alternating AT.

The CD signal for BO in presence of ctDNA was only weakly negative (data not shown) and this further illustrates the different binding mode of BEBO compared to BO.

POLYNUCLEOTIDE BINDING PREFERENCES

Figure 5A:
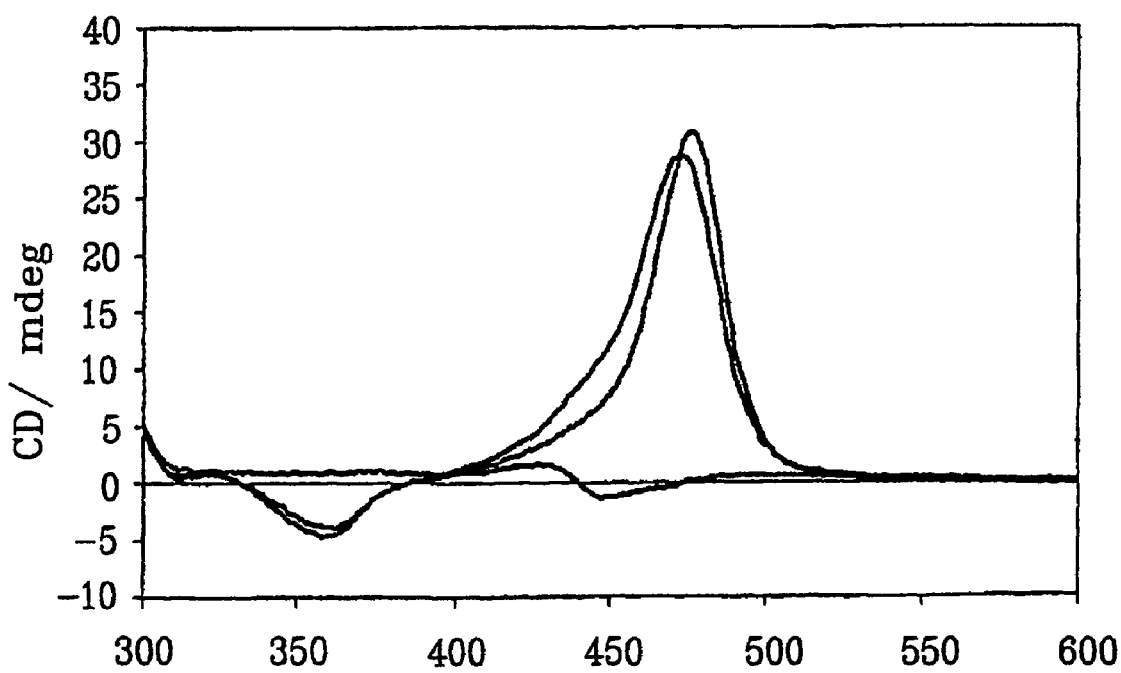
FIG. 5a-b. Change in CD after addition of [poly (dA-dT)]$_2$ into samples of BEBO in presence of (a) [poly (dG-dC)]$_2$ and (b) ctDNA (R=0.05 in both figures). [poly (dA-dT)]$_2$ was added to give mixing ratios, dye: AT-bases of; (a) (B) 0.1 and (C) 0.05, (b) from bottom to top: 0.1, 0.05 and 0.025. [dye]=11 μM in all spectra.

The extensive difference in amplitude of the CD signal for BEBO in the presence of poly-GC and poly-AT allowed a simple experiment to investigate a possible AT preference. When poly-AT was added to a sample of BEBO in the presence of poly-GC (R=0.05) the CD signal increased drastically, showing a considerable preference for poly-AT (FIG. 5a). These spectra were consistent with the CD spectra of BEBO in the presence of poly-AT without poly-GC (FIG. 4a) with only slightly lower amplitudes of the signals.

Figure 5B:
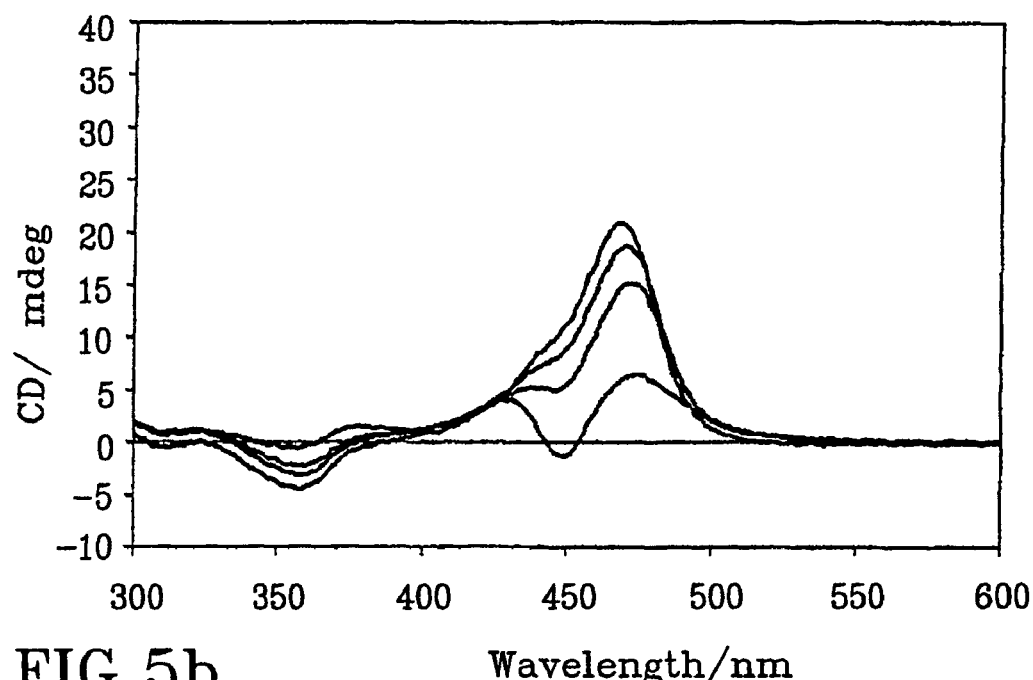

A similar experiment was performed to compare the binding affinities of BEBO to poly-AT and ctDNA. Again poly-AT was added to a sample of BEBO now in the presence of ctDNA. There was an increase in CD signal upon addition of poly-AT but not as large as when the sample initially contained poly-GC (FIG. 5b). Hence, there is still a reasonable amount of dye bound to ctDNA at these ratios, showing that there must be other binding sites than alternating AT-regions in ctDNA that attract BEBO significantly.

FLUORESCENCE AND ABSORBANCE MEASUREMENTS

The absorption and fluorescence properties of BEBO with different nucleic acids are summarised in table 1. In analogy with other asymmetric cyanine dyes BEBO has a large increase in fluorescence upon binding to DNA. The clear minor groove binding of BEBO to poly-AT affords a 180-fold enhancement in fluorescence intensity, whereas the increases upon binding to ctDNA and poly-GC are somewhat larger. In buffer solution, the free dye has its emission peak at 542 nm compared to 492 nm for the bound dye. Using ethanol instead of aqueous buffer as solvent, the free dye emission was shifted to 492 nm, and the fluorescence intensity was roughly ten times lower. Recently, aggregation of TO in the presence and absence of DNA was studied by absorption and fluorescence spectroscopy and similar manifestations caused by aggregate formation was seen.[30] Thus, in buffer solution, dimers or higher aggregates with longer emission maximum are probably formed due to the hydrophobic nature of the dye.

Figure 6A:
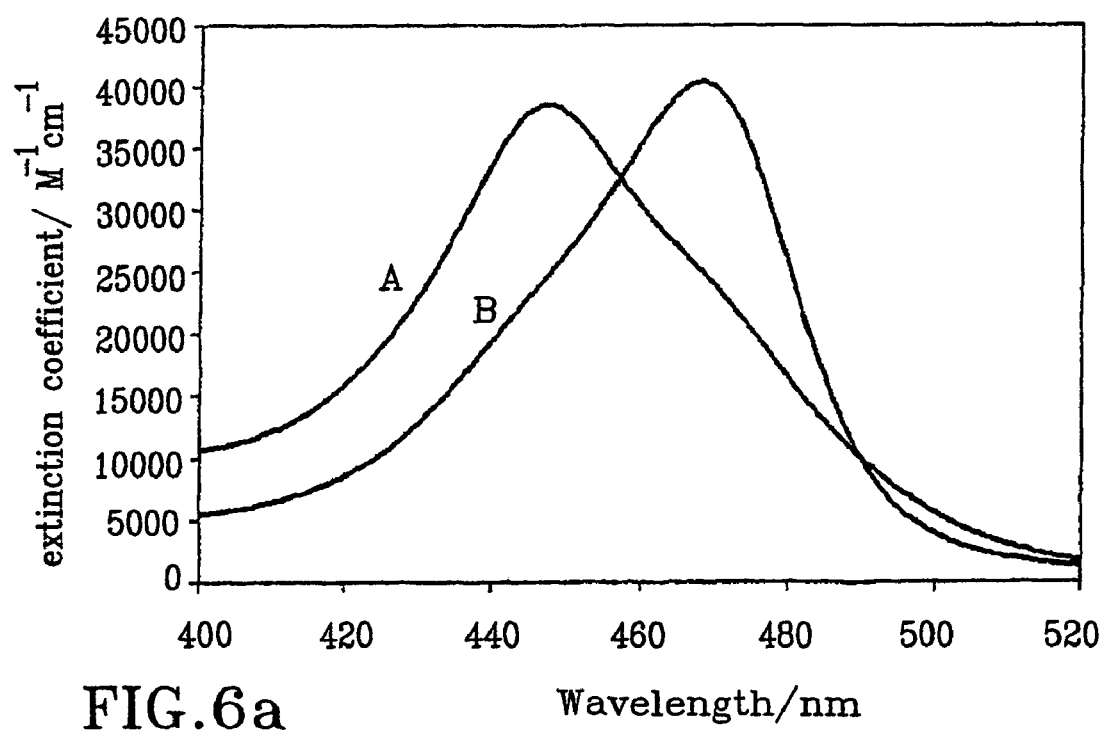
FIG. 6a-b. (a): Absorption spectra of BEBO free in buffer (A) and bound to calf thymus DNA (B) at R value of 0.02. (b): Absorption spectra of free BEBO in water-methanol solutions with different compositions ranging from 0 to 100% methanol (thickened lines).
Figure 6B:
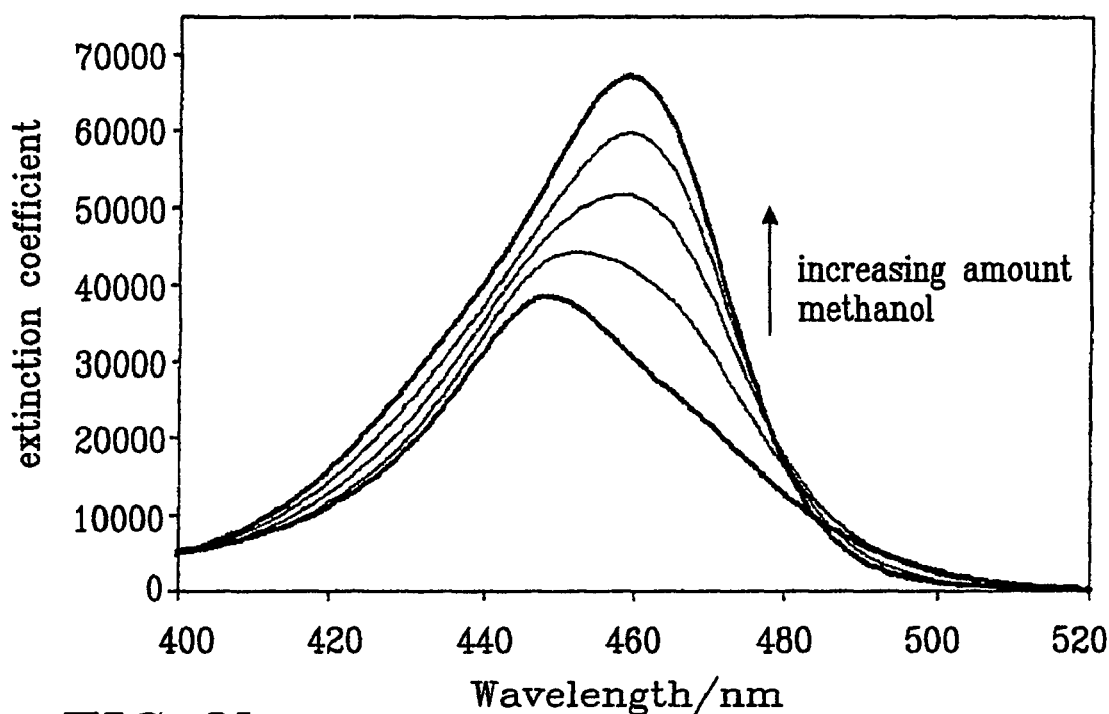
Figure 7A:
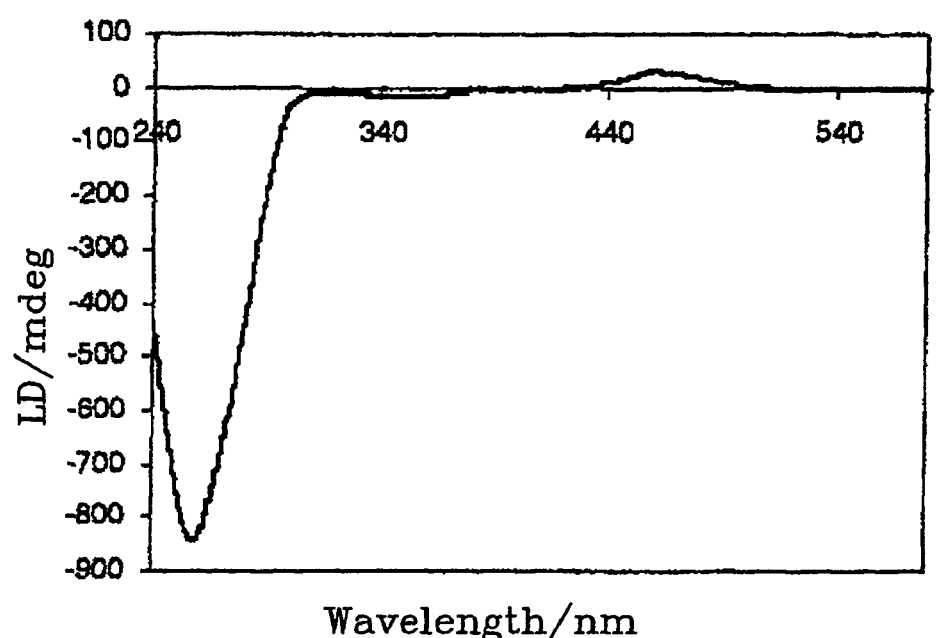
FIG. 7. Flow LD spectra of BEBO complexed with: calf thymus DNA (top left), poly[dA-dT]$_2$ (bottom left), poly[dG-dC]$_2$ (bottom right), and BO complexed with calf thymus (top right). Mixing ratios (R=dye/DNA bases) were 0.05 in all cases except for poly [dG-dC]$_2$ (R=0.02).
Figure 7B:
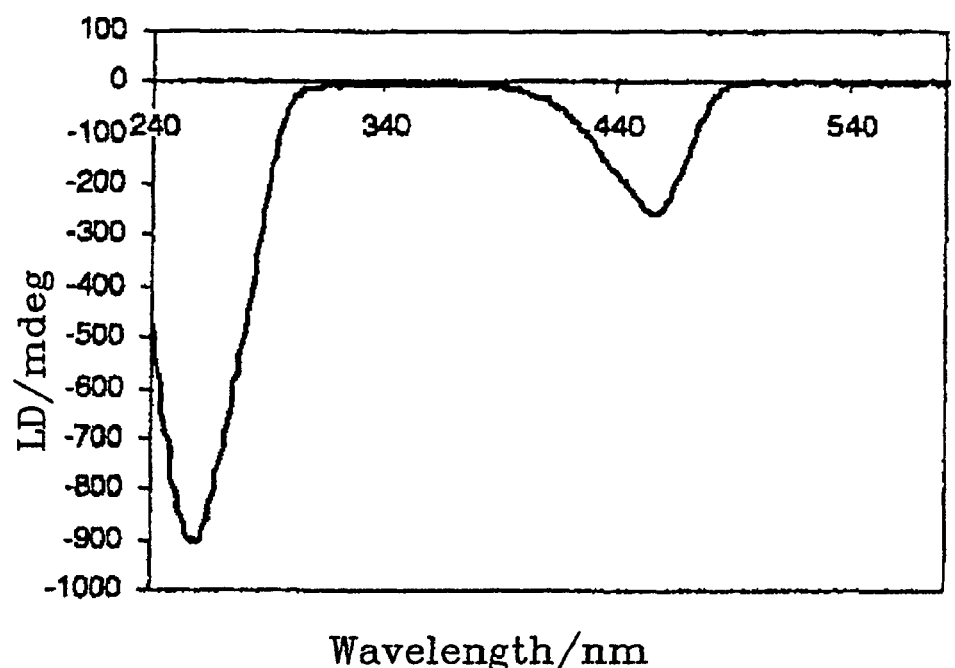
Figure 7C:
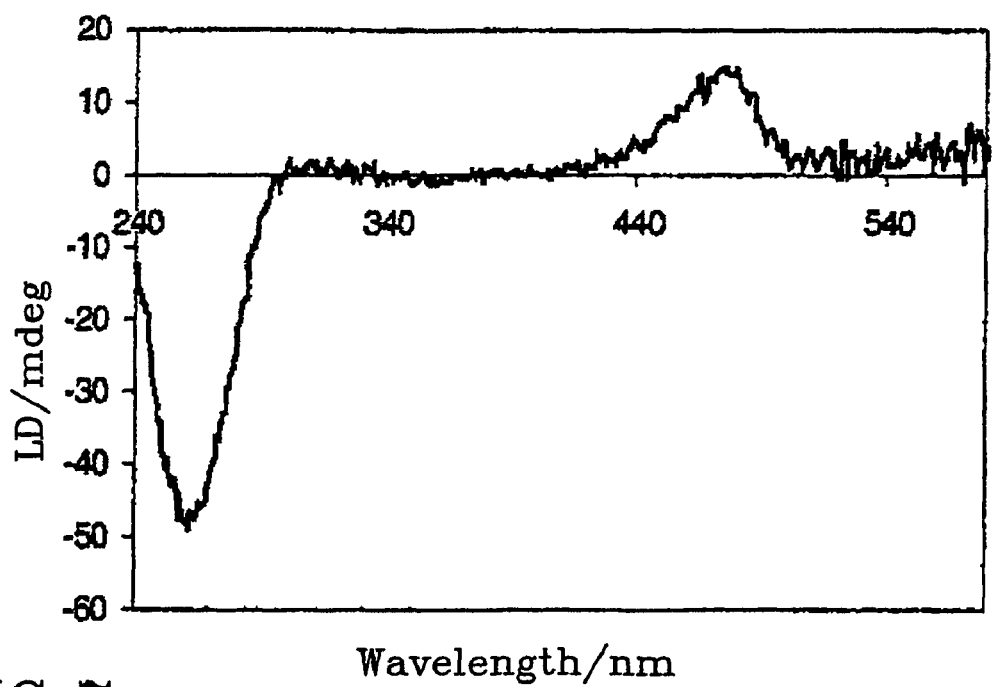
Figure 7D:
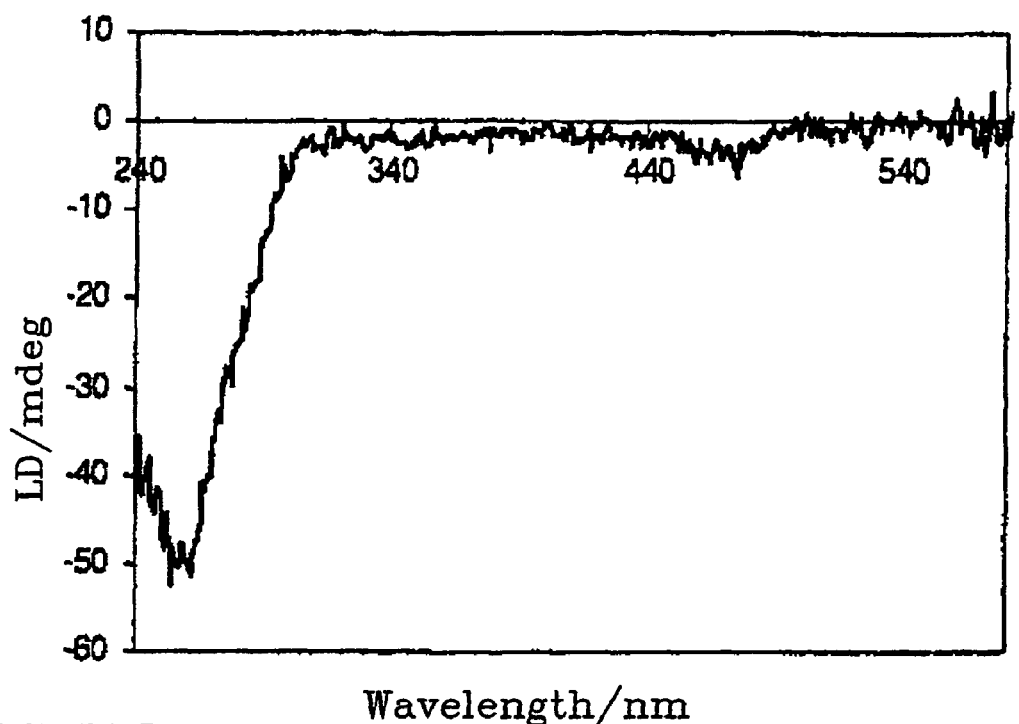

The shape of the absorption spectra of free BEBO in water further suggests the presence of dimers or aggregates (FIG. 6). Absorption measurements of BEBO in different methanol-water mixtures showed a substantial increase and a red shift in absorption with increasing amounts of methanol (FIG. 6b). The dye molecules are presumably present at monomers in pure methanol. The absorption spectrum of free BEBO in methanol and the spectrum of BEBO completely bound to DNA have a very similar shape, which indicates that the dye is bound as monomers at low binding ratios.

In summary, we find that the structural modifications of BO have induced a shift in binding mode from intercalation towards minor groove binding. Our results further imply the potential of the benzothiazole group as a minor groove recognition moiety. The dye could be synthesised in only four steps from the commercially available aniline 1. The binding of BEBO to poly-AT is clearly in the minor groove as deduced from the CD- and LD-spectra. Similarly to that of DAPI and Hoechst, the binding of BEBO to poly-GC is dominated by intercalation. With the random sequence ctDNA on the other hand, BEBO seems to interact heterogeneously. However, intercalation to GC-segments and minor groove binding to AT-regions cannot be the only explanation to the LD- and CD-results obtained with ctDNA. There must be other preferred binding sites in ctDNA for BEBO, which induce a lower CD than poly-AT. The relatively large amplitude of the CD signal show, however, that there is a significant contribution of minor groove binding of BEBO to ctDNA. Consistent with other minor groove binders, BEBO has a distinct preference for poly-AT compared to poly-GC. The fluorescence increase upon binding to the minor groove of poly-AT is larger than for Hoechst and DAPI. The binding properties of BEBO, in particular its strict minor groove binding to poly-AT, give promise for the development of a new class of asymmetric cyanine dyes with a strong preference for minor groove binding and a large increase in fluorescence upon binding.

EXPERIMENTAL EXAMPLE

Preparation According to the Reaction Scheme

The dye 1 was prepared in four steps starting from the commercially available aniline 1. Thiocyanation of the 4-substituted aniline 1 with potassium thiocyanate and bromine in DMF afforded the 2-aminobenzothiazole 2 in a 40% yield. Methylation and deprotonation of compound 2 proceeded in a total 70% yield to produce the 2-imino-3-methylbenzothiazoline 3. The dye 5 was prepared in 20% by melting compound 3 together with the pyridinium salt 4 at 160° C. under vacuum.

SYNTHESIS 2-(Tri-n-butylstannyl)-benzothiuole (1) and 2-(Tri-n-butylstannyl)-benzoxuole (2) was prepared by treating benzothiazole and benzoxazole, respectively with n-BuLi at −78° C., followed by addition of tri-n-butyltin chloride.

Scheme:
Preparation of the organostannanes.

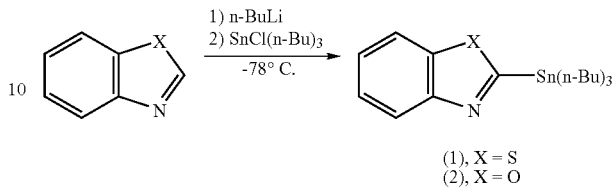

(1), X = S
(2), X = O

6-Bromo-2-methyl-benzothiazole (5)

2,4-Dibromo-aniline was treated with acetic anhydride in pyridine to give the acetanilide (3). Reaction of (3) with phosphorus pentasulfide in refluxing benzene replaced the carbonyl oxygen by a sulphur atom to give the thioacetanilide (4). Separation of (4) from (3) is readily achieved by extraction with aqueous NaOH. This is possible due to the fact that the sulphur atom is larger and more polarizable than the oxygen and thereby able to form the water-soluble thioacetaniline anion (4'). This ability to form (4') is also utilized in the final step, in which (4) is treated with sodium methoxide, and elimination of the bromine in 2 position leads to ring closure, giving the product (5). Upon removing the NMP by bulb-to-bulb distillation, it was discovered that (5) is easily purified by sublimation.

Scheme:
Preparation of (5) from 2,4-dibromo-aniline.

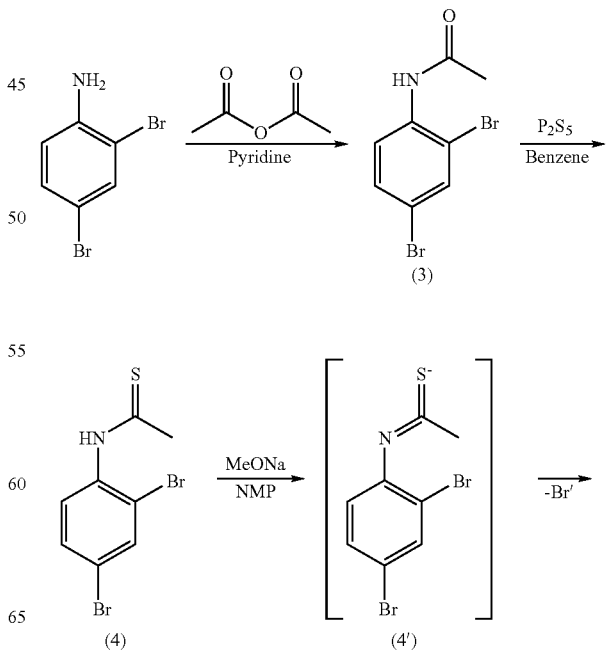

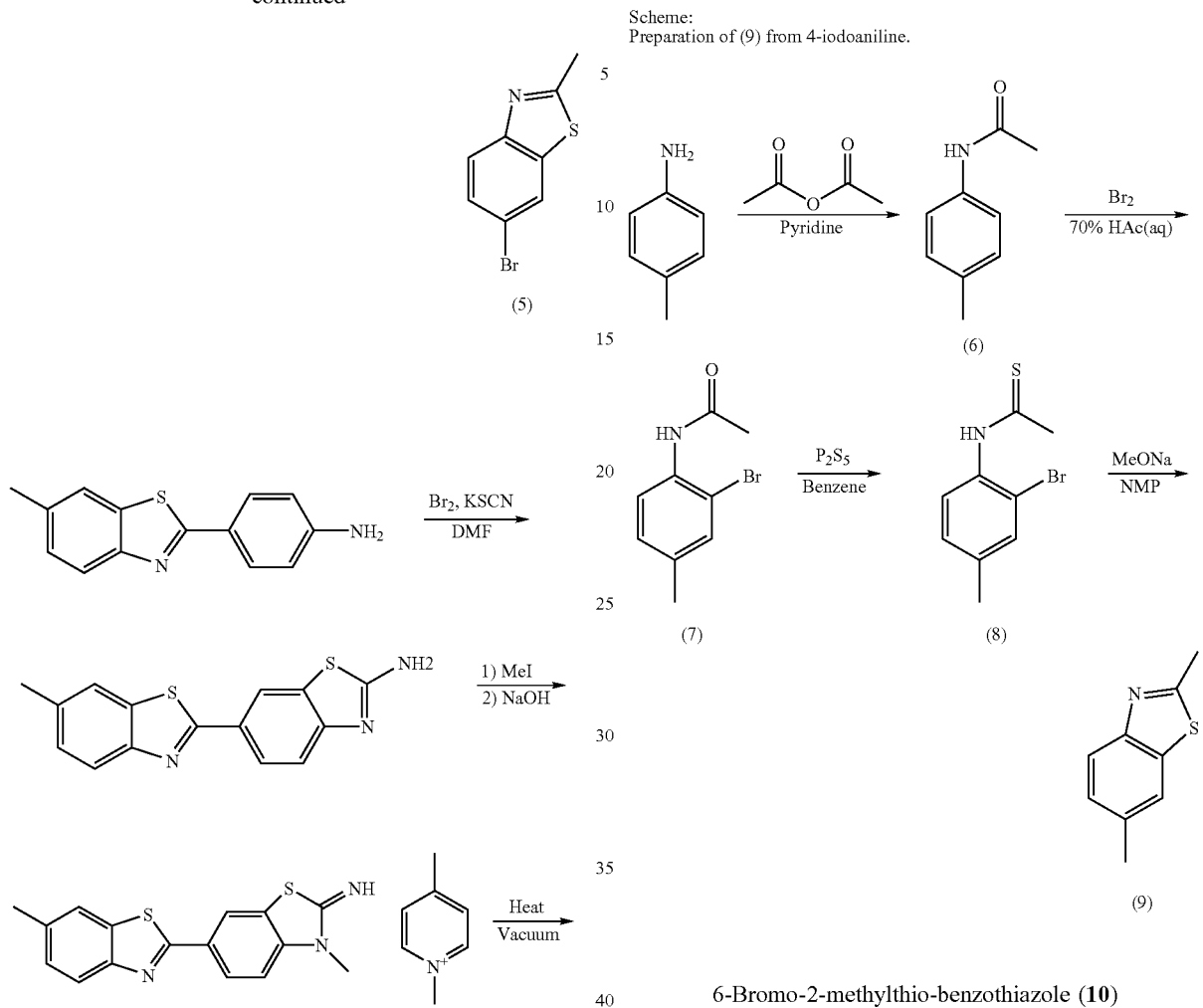

6-Iodo-2-methyl-benzothiazole (9)

The synthesis of (5) and its iodo analogue (9) are very similar. However, in this case the dihalogenated acetanilide (7) is achieved by acylation of 4-iodo-aniline to give (6), followed by bromination. In this bromination step, some of the iodine in the 4-position was substituted by bromine. Attempts to separate the formed 2,4-dibromo-acetanilide from (7) were fruitless, which resulted in a product mixture of (9) and (5) in a 3:1 molar ratio. In spite of this, the mixture was used in following Stille-coupling reactions.

6-Bromo-2-methylthio-benzothiazole (10)

Although not being used in our subsequent reactions, it should be mentioned that yet another halogenated electrophile, 6-Bromo-2-methylthio-benzothiazole (10), was prepared. The synthesis of (10) is, as seen in the following scheme, quite uncomplicated. 2-Methylthio-benzothiazole is simply brominated in acetic acid with FeCl$_3$ as catalyst.

Scheme:
Bromination in 6-position of 2-methylthio-benzthiazole

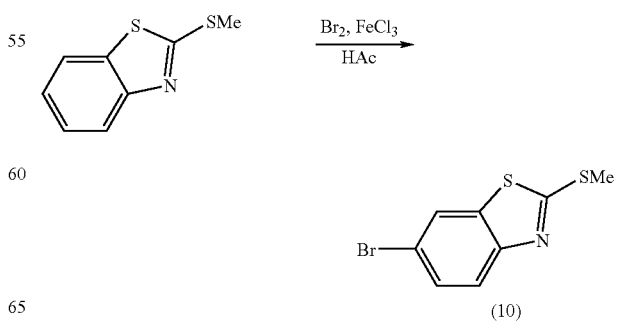

STILLE-COUPLINGS

To study and optimise the palladium catalysed cross-coupling reaction, a number of experiments were carried out with different starting materials and two different neutral ligands on the catalyst. However, the procedure describing the synthesis of (11) and (13) in the experimental section was followed in all Stille-couplings. CuI is used for its co-catalytic effect on the coupling. Table 1 summarises the Stille-experiments carried out during this work.

TABLE 1

A summary of the Stille-reactions performed.

| Entry | Organostannane | Arylhalide | Catalyst | Product | Yield |
|---|---|---|---|---|---|
| 1 | (1) | Br–C₆H₅ | Pd(PPh₃)₄ | benzothiazole-phenyl | Low |
| 2 | (1) | I–C₆H₅ | Pd(PPh₃)₄ | benzothiazole-phenyl | 72% |
| 3 | (1) | I–C₆H₅ | Pd(AsPh₃)₄ | benzothiazole-phenyl | 33% |
| 4 | (1) | Br-indole | Pd(PPh₃)₄ | benzothiazole-indole | 0% |
| 5 | (1) | (5) Br-methylbenzothiazole | Pd(PPh₃)₄ | (11) | 0% |
| 6 | (1) | (5) Br-methylbenzothiazole | Pd(AsPh₃)₄ | (11) | 0% |
| 7 | (1) | (9) I-methylbenzothiazole | Pd(AsPh₃)₄ | (11) | 0% |
| 8 | (1) | (9) I-methylbenzothiazole | Pd(PPh₃)₄ | (11) | 98% |
| 9 | (2) | (9) I-methylbenzothiazole | Pd(PPh₃)₄ | (13) | 95% |

In entry 1, pure product could not be isolated despite flash chromatography (chloroform on silica). However, a small amount of product was confirmed by mass spectrometry. The superior performance of iodine in comparison with bromine on the electrophiles has been previously reported, and was therefore expected. This property is given by iodine's greater ability to act as a leaving group. Another reason for the failed experiments in entries 4-7 might be that the nitrogen in 4-position to bromine donates its free electron pair into the arylring, thereby deactivating the electrophile. The reason for trying to use brominated electrophiles anyway was their more facile synthesis. Although the arylhalide in entries 8-9 in reality was a 3:1 (molar-) mixture of (9) and (5), the yields in table 1 we calculated with respect only to the amount of (9). This is due to the total reluctance of the brominated electrophiles in entries 4-7 to react.

Using triphenylarsine as the palladium-ligand has been reported to show up to a 1100-fold increase in reaction rates, compared to triphenylphosphine. Surprisingly though, triphenylarsine was less effective than triphenylphosphine in the experiments performed. This may, ironically enough, depend on triphenylarsine's superiority as ligand, which makes Pd(O) more liable to oxidate and the catalyst far more air-sensitive than the one with triphenylphosphirle. Hereby, a small contamination of air-oxygen in the reaction vessel might substantially decrease the catalytic effect of tripherrylarsine-coordinated palladium, whereas the catalyst with phosphine-ligand is less affected.

BETO & BOXTO

The two new asymmetric cyanine dyes BETO and BOXTO were prepared by the reaction paths shown in schemes 8 and 9.

Scheme.
The two final steps in the synthesis of BETO

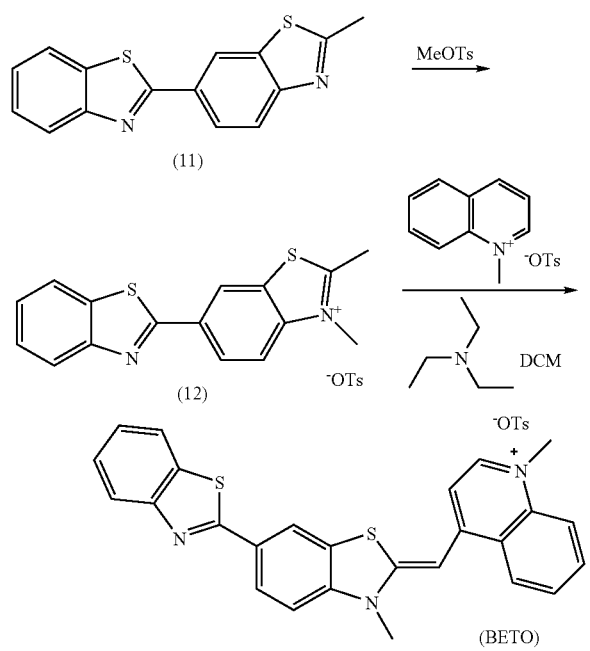

Scheme 9.
The final steps in the synthesis of BOXTO.

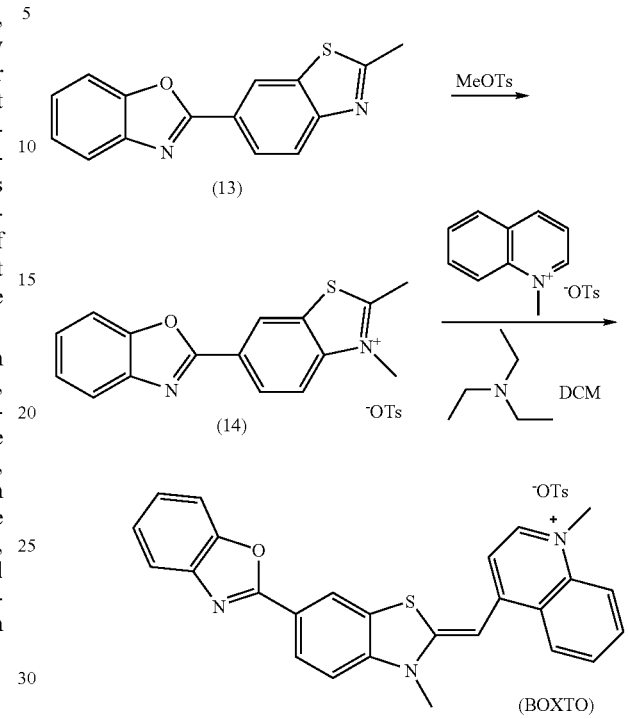

By treating (11) and (13) with an excess of melted methyl tosylate, the methylated salts (12) and (14) were formed in 70% and 56% yields respectively. These salts were allowed to react with 1-methyl-quinolinium tosylate in dichloromethane to produce the desired dyes. The yields in the last step were 27% and 30% respectively.

Column chromatography was performed using aluminium oxide (activated, neutral, approx. 150 mesh) deactivated by the addition of water to Brockman grade III. Melting points were determined on a Mettler FP82HT hot-stage microscope. $^1$H (400 MHz) and $^{13}$C (100.6 MHz) NMR spectra were recorded at rt using a Varian UNITY-400 NMR spectrometer. Chemical shifts are in ppm, relative to solvent peaks for DMSO ($\delta$ 2.50 for $^1$H and $\delta_C$ 39.51 for $^{13}$C NMR); J values are given in Hz. High resolution mass spectra were recorded using a VG ZabSpec instrument. UV-vis spectra were measured on a Varian Cary4 spectrophotometer. Fluorescence spectra were recorded using a SPEX fluorolog τ2 spectrofluorimeter. The LD and CD spectra were recorded on a JASCO-720 spectropolarimeter. The orientation of the DNA complexes was achieved using a flow Couette cell with outer rotating cylinder. All spectroscopic measurements were performed at 25° C. in 25 mM sodium phosphate buffer (pH 7.0). Aqueous solutions of BEBO and BO were typically obtained from 2 mM stock solutions in DMSO. [Poly (dA-dT)]$_2$ and [poly (dG-dC)]$_2$) were purchased as solutions in buffer from Pharmacia. Calf thymus DNA was purchased from Fluka. Commercial reagents were purchased from Sigma-Aldrich and used without further purification. The pyridinium salt 4 and the benzothiazolium salt 5 were prepared as previously reported.[23]

2-Amino-6-(6-methyl-benzothiazol-2-yl)-benzothiazole (2)

2-(4-aminophenyl)-6-methyl-benzothiazole 1 (4.0 g, 16.6 mmol) and KSCN (2.6 g, 26.7 mmol) were dissolved in DMF (20 ml) and cooled in an ice-bath. $Br_2$ (0.9 ml, 17 mmol) in DMF (15 ml) was added dropwise under 3 h. The mixture was stirred for another 20 h. Water was added and the precipitate formed was collected by filtration and dried. The crude product was triturated on the sinter with several portions of boiling dichloromethane to afford 2 as a light green-yellow solid (1.97 g, 40%). Mp 250-251° C.; $^1$H NMR (DMSO): δ 2.45 (3H, s, Ar—$CH_3$), 7.34 (1H, d, J=8.4, ArH), 7.50 (1H, d, J=8.4, ArH), 7.89 (1H, d, J=8.4, ArH), 7.91 (1H, s, ArH), 7.99 (1H, d, J=8.4, ArH), 8.51 (1H, s, ArH), 8.56 (2H, s, $NH_2$); $^{13}$C NMR (DMSO): δ 21.10, 116.7, 120.7, 121.8, 122.1, 125.6, 126.9, 128.1, 129.7, 133.3, 134.5, 135.0, 151.7, 165.9, 169.3; HR-FAB-MS m/z Found: 298.0521 $C_{15}H_{12}N_3S_2$ (M+H$^+$): requires M, 298.0473.

2-Amino-3-methyl-6-(6-methyl-benzothiazol-2-yl)-benzothiazolium iodide

The 2-aminobenzothiazole 2 (0.3 g, 1.0 mmol) was dissolved in DMSO (2 ml). Methyl iodide (0.25 ml, 2.0 mmol) was added and the mixture was stirred at 110° C. for 17 hours. The mixture was cooled and poured into water. The precipitate formed was collected by filtration and washed with water to give the product as a yellow solid (0.38 g, 86%). Mp 267-269° C.; $^1$H NMR (DMSO): δ 2.47 (3H, s, Ar—$CH_3$), 3.74 (3H, s, N—$CH_3$), 7.38 (1H, d, J=8.4, ArH), 7.79 (1H, d, J=8.4, ArH), 7.93 (1H, d, J=8.4, ArH), 7.95 (1H, s, ArH), 8.22 (1H, d, J=8.4, ArH), 8.75 (1H, s, ArH), 10.19 (2H, s, $NH_2$); $^{13}$C NMR (DMSO): δ 21.14, 32.39, 113.9, 122.0, 122.2, 122.4, 122.7, 126.6, 128.3, 129.8, 134.7, 135.6, 140.9, 151.6, 164.7, 168.9; HR-FAB-MS m/z Found: 312.0638 $C_{16}H_{14}N_3S_2$ (M$^+$): requires M, 312.0629.

2-Imino-3-methyl-6-(6-methyl-benzothiazol-2-yl)-benzothiazoline (3)

2-amino-3-methyl-6-(6-methyl-benzothiazol-2-yl)-benzothiazolium iodide (0.3 g, 0.68 mmol) was taken up in DMSO (10 ml). Water was added (20 ml) and the mixture was basified to pH 10 with aqueous NaOH (20%). The precipitate was collected by filtration and washed with water to produce 3 as a light yellow solid (0.19 g, 89%). Mp 146-148° C.; $^1$H NMR (DMSO): 2.45 (3H, s, Ar—$CH_3$), 3.38 (3H, s, N—$CH_3$), 7.16 (1H, d, J=8.4, ArH), 7.33 (1H, d, J=8.4, ArH), 7.87 (1H, s, ArH), 7.90 (1H, s; ArH), 7.93 (1H, d, J=8.4, ArH), 8.16 (1H, s, ArH), 8.55 (1H, s, NH); $^{13}$C NMR analysis was not possible due to poor solubility of 4 in available deuterated solvents; HR-FAB-MS m/z Found: 312.0619 $C_{16}H_{14}N_3S_2$ (M+H$^+$): requires M, 312.0629.

4-[(3-Methyl-6-(6-methyl-benzothiazol-2-yl)-2,3-dihydro-(benzo-1,3-thiazole)-2-methylidene)]-1-methyl-pyridinium iodide (BEBO)

The benzothiazoline 3 (0.1 g, 0.32 mmol) and 1,4-dimethyl-pyridium tosylate 4 was melted together at 160° C. under vacuum for 1 hour. DMSO (5 ml) was added and the mixture was heated at reflux for 30 min. The mixture was added to aqueous KI (30%) and the precipitate formed was collected by filtration. The solid was purified by flash chromatography on neutral $Al_2O_3$ with methanol-dichloromethane (2:98) to give BEBO (0.04 g, 24%). Mp 280-281° C.; $^1$H NMR (DMSO): δ 2.47 (3H, s, Ar—$CH_3$), 3.76 (3H, s, N—$CH_3$), 4.02 (3H, s, N—$CH_3$), 6.34 (1H, s, =CH—), 7.38 (1H, d, J=8.4, ArH), 7.47 (1H, d, J=6.8, PyH), 7.70 (1H, d, J=8.4, ArH), 7.93 (1H, d, J=8.4, ArH), 7.95 (1H, s, ArH), 8.18 (1H, d, J=8.4, ArH), 8.39 (1H, d, J=6.8, PyH), 8.65 (1H, s, ArH); $^{13}$C NMR (DMSO): 21.13, 32.99, 45.11, 90.66, 112.0, 118.8, 120.9, 121.8, 122.2, 124.6, 126.7, 127.9, 128.1, 134.5, 135.2, 142.4, 142.5, 150.1, 151.6, 156.4, 164.9; HR-FAB-MS m/z Found: 402.1145 $C_{23}H_{20}N_3S_2$ (M$^+$): requires M, 402.1105.

2-(Tri-n-butylstannyl)-benzothiazole (1)

20 ml of freshly distilled THF was flushed for 30 min with a stream of nitrogen after which benzothiazole (1.0 g, 7.4 mmol) was added. After being flushed for another 30 min, the solution was cooled to −78° C. and placed under inert nitrogen atmosphere. 0.9 equivalents of n-BuLi (2 M solution in hexane, 2.66 ml, 6.66 mmol) was added dropwise over a period of 30 min, during which the solution turned to deep red. The solution was kept at −78° C. for 1 h and then tri-n-butyltin chloride (2.0 mi, 7.4 mmol) was added dropwise over a period of 1 h. During this addition, the solution shifted from deep red to brownish yellow, then to greenish blue and finally to light brown. After yet another hour at −78° C., the solution was allowed to reach room temperature. The THF was removed on a rotary evaporator and the product, a yellow oil, was isolated by distillation in vacuo. Yield: 2.47 g, 79%. $^1$H NMR (CDCl$_3$): δ 0.90 (t, J=S, 9H, $Bu_3Sn$), 1.29 (in, 6H, $Bu_3Sn$), 1.35 (m, 6H, $Bu_3Sn$), 1.63 (t, J=8, 6H, $Bu_3Sn$), 7.37 (t, J=8, 1H, ArH), 7.46 (t, J=8, 1H, ArH, 7.96 (d, J=8, 1H, ArH), 8.17 (D, J=8, 1H, ArH).

2-(Tri-n-butylstannyl)-benzoxazole (2)

20 ml of freshly distilled THF was flushed for 30 min with a stream of nitrogen after which benzoxazole (1.0 g, 8.3 mmol) was added. After being flushed for another 30 min, the solution was cooled to −78° C. and placed under inert nitrogen atmosphere. 0.9 equivalents of n-BuLi (2 M solution in hexane, 3.0 ml, 7.6 mmol) was added dropwise over a period of 1 h, during which the solution turned to pink. The solution was kept at −78° C. for 30 min and then tri-n-butyltin chloride (2.3 ml, 8.3 mmol) was added dropwise over a period of 1 h. During this addition, the solution shifted from pink to brown. After yet another hour at −78° C., the solution was allowed to reach room temperature, at which it turned to deep red. The THF was removed on a rotary evaporator and the product, an orange oil, was isolated by distillation in vacuo. Yield: 1.37 g, 40%. $^1$H NMR (CDCl$_3$): δ 0.90 (t, J=7, 9H, $Bu_3Sn$), 1.30 (m, 6H, $Bu_3Sn$), 1.35 (m, 6H, $Bu_3Sn$), 1.62 (t, J=7, 6H, $Bu_3Sn$), 7.29 (t, 2H, ArH), 7.55 (d, 1H, ArH), 7.77 (d, 1H, ArH).

2,4-Dibromo-acetanilide (3)

A solution of 2,4-Dibromo-aniline (3.0 g, 12.0 mmol), 1.1 equivalents of acetic anhydride (1.35 g, 13.2 mmol) and pyridine (0.95 g, 12.0 mmol) was heated to 100° C. After a few minutes, a precipitate had formed and pyridine (~3 ml) was added to dissolve the precipitate. The solution was kept at 100° C. for two hours after which it was allowed to cool to room temperature and was poured into water. The precipitate formed was collected by filtration and washed with water to give the product as a white powder in quantitative yield (3.9 g, slightly wet) $^1$HNMR (CDCl$_3$): δ 2.24 (a, 3H, —$CH_3$), 7.43 (d, $J_1$=8.8, $J_2$=2, 1H, ArH) 7.69 (s, J=2, 1H, ArH) 8.27 (d, J=8.8, 1H, ArH).

2,4-Dibromo-thioacetanilide (4)

2,4-Dibromo-acetanilide (2.2 g, 7.51 mmol) was dissolved in 10 ml benzene and phosphorus pentasulfide (3.34 g, 7.51 mmol) was added. The mixture was refluxed at 80° C. After a few minutes, a gummy solid was formed at the bottom of the flask. To suspend the solid and make stirring possible, an additional 20 ml of benzene was added and the mixture was swirled vigorously. After refluxing for 5.5 h, thin layer chromatography (TLC) on silica in chloroform suggested complete reaction and the heating was removed. After cooling to room temperature, the brownish slurry was filtered and the precipitate washed with diethyl ether. The benzene/ether filtrate was extracted twice with NaOH, (10%). The basic, aqueous phase was acidified to pH ~1 with conc. HCl. This gave a light brown, milky slurry. The precipitate could not be collected by filtration and the slurry was therefore extracted twice with diethyl ether. This resulted in a yellow organic phase, which was dried and evaporated to give the thioacetanilide as a brown, yellowish oil. Yield: 1.33 g, 57%. $^1$HNMR (CDCl$_3$): δ 2.78 (S, 3H, —CH$_3$), 7.50 (d, $J_1$=8.8, $J_2$=1.6, 1H, ArH) 7.90 (s, J=1.6, 1H, ArH) 8.40 (d, J=8.8, 1H, ArH).

6-Bromo-2-methyl-benzothiazole (5)

2,4-Dibromo-thioacetanilide (1.33 g, 4.3 mmol) and 1.2 equivalents of sodium methoxide (0.513 g, 5.2 mmol) was dissolved in 3 ml NMP After 2 h at 150° C. and cooling to room temperature, the NMP was removed by bulb-to-bulb distillation. The brown remnants were purified by sublimination to give the product as white crystals. Yield: 707 mg, 72%. $^1$H NMR (CDCl$_3$): δ 2.83 (s, 3H, —CH$_3$), 7.55 (d, $J_1$=8.8, $J_2$=1.6, 1H, ArH) 7.80 (d, J=8.8, 1H, ArH) 7.96 (s, J=1.6, 1H, ArH).

4-Iodo-acetanilide (5)

4-Iodo-aniline (5.0 g, 22.8 mmol) and 1.1 equivalents of acetic anhydride (2.56 g, 25.1 mmol) was dissolved in 3 ml pyridine. After 2 h at 100° C., TLC suggested complete reaction and the heat was removed. When the solution had reached room temperature, it was poured into water. The precipitate formed was collected by filtration and washed with water to give the product as a white powder. Yield: 5.86 g, 98%. $^1$H NMR (DMSO): δ 2.03 (s, 3H, —CH3), 7.41 (d, J=8.8, 2H, ArH) 7.61 (d, J=8.8, 2H, ArH) 10.03 (s, 1H, NH).

2-Bromo-4-iodo-acetanilide (7)

To a solution of 4-Iodo-acetanilide (3.74 g, 14.3 mmol) in 20 ml HAc$_{aq}$., (70%), 1.1 equivalents of bromine (2.53 g, 15.7 mmol) was added dropwise. After being allowed to react at 70° C. for 10 min, the solution was poured into water and the formed precipitate was collected by filtration (3.02 g). $^1$H NMR showed a mixture of the desired product and 2,4-dibromo-acetanilide in a 9:4 molar ratio. Total yield: 3.02 g, 65%. Yield of the desired product: 2.18 g, 45%. $^1$H NMR (CDCl$_3$): δ 2.23 (s, 3H, —CH3), 7.60 (d, $J_1$=8.8, $J_2$=1.6, 1H, ArH) 7.85 (s, J=1.6, 1H, ArH) 8.13 (d, J=8.8, 1H, ArH). Yield of the by-product: 0.84 g, 20%. $^1$H NMR (CDCl$^3$): Consistent with the spectrum of 2,4-dibromo-acetanilide described above.

2-Bromo-4-iodo-thioacetanilide (8)

A total amount of 2.87 g of the 2-Bromo-4-iodo-acetanilide (2.08 g, 6.1 mmol) and 2,4-dibromo-acetanilide (0.80 g, 2.7 mmol) mixture was dissolved in ~10 ml benzene and phosphorus pentasulfide (3.75 g, 8.4 mmol) was added. The mixture was refluxed at 80° C. over a period of 2 h. After being allowed to cool to room temperature, the brown slurry was filtered and the precipitate washed with diethyl ether. The benzene/ether filtrate was extracted twice with NaOH, (10%) and the basic, aqueous phase was acidified to pH ~1 with conc. HCl. This gave a light brown, milky slurry, which was extracted twice with diethyl ether and resulted in a yellow organic phase. This phase was dried and evaporated to give a mixture of 2-bromo-4-iodo-thioacetanilide and 2,4-dibromo-thioacetanilide as a brown oil. Total yield: 2.14 g, 71%. Yield of desired product: 1.66 g, 77%. $^1$H NMR (CDCl$_3$): δ 2.78 (S, 3H, —CH$_3$), 7.68 (d, 1H, ArH) 7.96 (s, 1H, ArH) 8.29 (d, 1H, ArH). Yield of the by-product: 480 mg, 57%. $^1$H NMR (CDCl$_3$): Consistent with the spectrum of 2,4-dibromo-thioacetanilide described above.

6-Lodo-2-methyl-benzothiazole (9)

A total amount of 2.02 g of the mixture of 2-bromo-4-iodo-thioacetanilide (1.57 g, 4.4 mmol) and 2,4-dibromo-thioacetanilide (454 g, 1.5 mmol) was dissolved in 15 ml NMP. Sodium methoxide (0.677 g, 6.9 mmol) was added and the mixture was stirred at 150° C. for 2.5 h. When the brown solution had cooled to room temperature, the NMP was removed by bulb-to-bulb distillation. The brown remnants were purified by sublimation to give a mixture of 6-iodo-2-methyl-benzothiazole and 6-bromo-2-methyl-benzothiazole (molar ratio 3:1) as white crystals. Total yield: 1.33 g, 86%. Yield of desired product: 1.04 g, 86%. $^1$H NMR (CDCl$_3$): δ 2.82 (s, 3H, —CH3), 7.68 (d, J=8.4, 1H, ArH) 7.73 (d, J=8.4, 1H, ArH) 8.16 (a, 1H, ArH). Yield of the by-product: 289 mg, 86%. $^1$H NMR (CDCl$^3$) Consistent with the spectrum of 6-bromo-2-methyl-benzothiazole described above.

6-Bromo-2-methylthio-benzothiazole (10)

To a solution of 2-methylthio-benzothiazole (1.14 g, 6.3 mmol) and bromine (1.24 g, 7.7 mmol) in 10 ml acetic acid, a catalytic amount of FeCl$_3$ was added. After being refluxed at 120° C. over a period of 4 h the orange reaction mixture was allowed to cool to room temperature and was then poured into ethyl acetate. The precipitate formed was collected by filtration, washed with ethyl acetate and refluxed for 1 h in ethyl acetate. This slurry was filtered and ethyl acetate was removed from the filtrate by rotary evaporation to give the product as yellow crystals (130 mg, 0.50 mmol). The precipitate, collected by filtration from the refluxed slurry, was Soxhlett-extracted with n-pentane followed by diethyl ether. Evaporation of the solvents produced another small amount of the desired product (70 mg, 27 mmol). Total yield: 200 mg, 0.77 mmol, 12%. $^1$H NMR (DMSO): δ 2.79 (s, 3H, —SCH3), 7.61 (d, $J_1$=8.8, $J_2$=2, 1H, ArH) 7.77 (d, J=8.8, 1H, ArH) 8.32 (s, J=2, 1H, ArH).

2-Methyl-6-(benzothiazol-2-yl)-benzothiazole (11)

216 mg of the mixture of 6-iodo-2-methyl-benzothiazole (169 mg, 0.61 mmol) and 6-bromo-2-methyl-benzothiazole (47 mg, 0.20 mmol) was dissolved in 10 ml DMF. The solution was flushed 30 min with nitrogen and Pd$_2$dba$_3$ (21 mg, 0.02 mmol) followed by addition of tri-phenylphosphine (46 mg, 0.18 mmol). After another 15 min of flushing, CuI (45 mg, 0.24 mmol) was added and the mixture was flushed for yet another 15 min and placed under inert nitrogen atmosphere. 2-(Tri-n-butylstannyl)-benzothiazole (500 mg, 1.18 mmol) was added and the mixture was heated to 60° C. After being kept at 60° C. for 6 h, the reaction mixture was allowed to cool to room temperature. The DMF was removed by bulb-to-bulb distillation to give a dark, yellow oil. This oil was purified by flash chromatography on silica with chloroform to produce the product as pink crystals. Yield: 169 mg, 74% (calculated with respect to total amount of 6-halogenated 2-methyl-benzothiazole), 98% (calculated with respect only to the amount of 6-iodo-2-methyl-benzothiazole). $^1$H NMR (CDCl$_3$): δ 2.89 (a, 3H, —CH$_3$), 7.41 (t, J=7.6, 1H, ArH), 7.52 (t, J=7.6, 1H, ArH, 7.93 (d, J=7.6, 1H, ArH), 8.03 (d, J=8.4, 1H, ArH), 8.09 (d, J=8.8, 1H, ArH), 8.15 (d, J=8.4, 1H, ArH) 8.64 (s, 1H, ArH). HR-FAB^-MS m/z Found: 283.038 C$_{15}$H$_{11}$N$_2$S$_2$ (M+H$^+$): requires M, 283.036.

2-Methyl-3-methyl-6-(benzothiazol-2-yl)-benzothiazolium tosylate (12)

2-methyl-6-(benzothiazol-2-yl)-benzothiazole (44 mg, 0.156 mmol) was stirred for 5 h at 90° C. in melted methyl tosylate (660 mg, 3.5 mmol). After being allowed to cool to room temperature, the product was precipitated by addition of acetone and collected by filtration. The precipitate was washed with acetone and allowed to dry over night. This gave the product as green crystals. Yield: 51 mg, 70%. $^1$H NMR (DMSO): δ 2.28 (s, 3H, —CH$_3$), 3.20 (s, 3H, CH$_3$), 4.24 (s, 3H, —CH$_3$), 7.11 (d, J=7.2, 2H, ArH), 7.46 (d, J=7.2, 2H, ArH), 7.55 (t, J=7.6, 1H, ArH), 7.62 (t, J=7.6, 1H, ArH), 8.14 (d, J=8, 1H, ArH), 8.25 (d, J=8, 1H, ArH), 8.45 (d, J=8.8, 1H, ArH), 8.59 (d, J=8.8, 1H, ArH), 9.24 (s, 1H, ArH). HR-FAB-MS m/z Found: 297.067 C$_{16}$H$_{13}$N$_2$S$_2$ (M$^+$): requires M, 297.052.

4-[(3-Methyl-6-(Benzothiazol-2-yl)-2,3-dihydro-(benzo-1,3-thiazole)-2-methylidene)]-methyl-quinolinium tosylate (BETO)

2-methyl-3-methyl-6-(benzothiazol-2-yl)-benzothiazolium tosylate (17 mg, 36 μmol) and 1-methyl-quinolinium tosylate (12 mg, 36 μmol) was dissolved in 2 ml dichloromethane. 2 equivalents of triethyl amine (10 μl, 72 μmol) was added and the deep red solution was allowed to react at room temperature over a period of 48 h, during which it turned to a brownish slurry. BETO was isolated as a red solid, by flash chromatography on neutral Al$_2$O$_3$ with methanol-dichloromethane (2:98). Yield: 6 mg, 27%. $^1$H NMR (Methanol-D$_4$): δ 3.64 (s, 3H, —CH$_3$), 3.83 (s, 3H, —CH$_3$), 6.14 (s, 1H, CH), 6.71 (d, J=6.8, 1H, ArH), 6.91 (t, J=7.2, 1H, ArH), 7.02 (t, J=7.2, 1H, ArH), 7.29 (m, 3H, ArH), 7.50 (m, 2H, ArH), 7.67 (t, J=7.2, 1H, ArH), 7.72 (d, J=8.8, 1H, ArH), 7.97 (s, 1H, ArH), 8.02 (d, J=6.4, 1H, ArH), 8.09 (d, J=8.4, 1H, ArH). HR-FAB-MS m/z Found: 438.118 C$_{26}$H$_{20}$N$_3$S$_2$ (M): requires M, 438.110.

2-Methyl-6-(benzoxazol-2-yl)-benzothiazole (13)

216 mg of the mixture of 6-iodo-2-methyl-benzothiazole (169 mg, 0.61 mmol) and 6-bromo-2-methyl-benzothiazole (47 mg, 0.20 mmol) was dissolved in 10 ml DMF. The solution was flushed 30 min with nitrogen and Pd$_2$dba$_3$ (21 mg, 0.02 mmol), tri-phenylphosphine (46 mg, 0.18 mmol) and CuI (45 mg, 0.24 mmol) was added. The mixture was flushed for another 15 min and placed under inert nitrogen atmosphere. 2-(Tri-n-butylstannyl)-benzoxazole (481 mg, 1.18 mmol) was added and the mixture was heated to 60° C. After being kept at 60° C. for 7 h, the reaction mixture was allowed to cool to room temperature. The DMF was removed by bulb-to-bulb distillation. The remaining oil was purified by flash chromatography on silica with chloroform to produce the product as red crystals. Yield: 154 mg, 71% (calculated with respect to total amount of 6-halogenated 2-methyl-benzothiazole), 95% (calculated with respect only to the amount of 6-iodo-2-methyl-benzothiazole). $^1$H NMR (CDCl$_3$): δ 2.89 (s, 3H, —CH$_3$), 7.37 (m, 2H, ArH), 7.59 (m, 1H, ArH), 7.78 (m, 1H, ArH), 8.06 (d, J=8.8, 1H, ArH), 8.40 (d, J=8.8, 1H, ArH), 8.75 (s, 1H, ArH). HR-FAB-MS m/z Found: 267.058 C$_{15}$H$_{11}$N2OS (M+H$^+$): requires M, 267.059.

2-Methyl-3-methyl-6-(benzoxazol-2-yl)-benzothiazolium tosylate (14)

2-methyl-6-(benzoxazol-2-yl)-benzothiazole (50 mg, 0.22 mmol) was stirred for 3 h at 90° C. in m excess of melted methyl tosylate (900 mg, 4.78 mmol). After being allowed to cool to room temperature, the product was precipitated by addition of acetone and collected by filtration. The precipitate was washed with acetone and allowed to dry over night. This gave the product as light brown crystals. Yield: 56 mg, 56%. $^1$H NMR (DMSO): δ 2.27 (s, 3H, CH$_3$), 3.21 (s, 3H, —CH$_3$), 4.24 (s, 3H, —CH$_3$), 7.09 (d, J=8, 2H, ArH), 7.47 (M, 4H, ArH), 7.88 (t, J=8.8, 2H, ArH), 8.49 (d, J=8.8, 1H, ArH), 8.64 (d, J=8.8, 1H, ArH), 9.32 (a, 1H, ArH). HR-FAB-MS m/z Found: 281.078 C$_{16}$H$_{13}$N$_2$OS (M$^+$): requires M, 281.075.

4-[(3-methyl-6-(benzoxazol-2-yl)-2,3-dihydro-(benzo-1,3-thiazole)-2-methylidene)]-1-methyl-quinolinium tosylate (BOXTO)

2-methyl-3-methyl-6-(benzoxazole-2-yl)-benzothiazolium tosylate (20 mg, 44 μmol) and 1-methyl-quinolinium tosylate (14 mg, 44 μmol) was dissolved in 2 ml dichloromethane. Triethyl amine (10 μl, 72 μmol) was added and the clear, red solution was allowed to react at room temperature over a weekend, during which it turned to a brownish red slurry. BOXTO was isolated as a red solid, by flash chromatography on neutral Al$_2$O$_3$ with methanol:dichloromethane (2:98). Yield: 8 mg, 30%. $^1$H NMR (Methanol-D$_4$): δ 3.74 (s, 3H, —CH$_3$), 3.97 (s, 3H, —CH$_3$), 6.33 (s, 1H, CH), 6.88 (d, J=6.8, 1H, ArH), 7.01 (m, 2H, ArH), 7.11 (d, J=7.2, 1H, ArH, 7.17 (d, J=7.2, 1H, ArH), 7.42 (d, J=7.2, 1H, ArH), 7.55 (t, J=8, 1H, ArH), 7.63 (d, J=8.4, 1H, ArH), 7.70 (t, J=7.6, 1H, ArH) 7.91 (d, J=8, 1H, ArH), 8.13 (a, 1H, ArH), 8.19 (d, J=6.8, 1H, ArH), 8.23 (d, J=8.4, 1H, ArH). HR-FAB-MS m/z Found: 422.134 C$_{26}$H$_{20}$N$_3$OS (M$^+$): requires M, 422.133.

| | Abs. Peak (nm) | Em. Peak (nm) | ΦF(c) | F$_{bound}$/F$_{free}$ (d) |
|---|---|---|---|---|
| Free BEBO | 448 | 542 | 0.011 | |
| BEBO-ctDNA (b) | 467 | 492 | 0.18 | 245 |

-continued

| | Abs. Peak (nm) | Em. Peak (nm) | φF(c) | $F_{bound}/F_{free}$ (d) |
|---|---|---|---|---|
| BEBO-polyAT (b) | 467 | 492 | 0.118 | 182 |
| BEBO-polyGC (b) | 471 | 492 | 0.226 | 264 |

(a) - Measured at at 25° C. in 10 mM sodium phosphate buffer (pH 7.0).
(b) - Dye:bases ratio of 1:100.
(c) - Fluorescence quantum yields, φF, were determined relative to fluorescein in 0.1M NaOH, assuming a φF of 0.93.
(d) - Increase in fluorescence intensity at 492 nm when exciting at 467 nm.

The minor groove-binding, asymmetric cyanine dye BEBO (above) has been evaluated using real-time PCR and compared with SYBR Green I. BEBO did not inhibit PCR at low concentrations and the fluorescence increase upon binding to dsDNA was sufficient for real-time measurement on the instruments used. Background fluorescence was caused by aggregation and it was approximately twice that of SYBR Green at optimized concentrations.

The fluorescence increase when binding to DNA was lower than for SYBR Green and caused a retardation of the curves and the Ct was delayed approximately 4 cycles compared to SYBR Green.

The similar dyes BETO and BOXTO both seem to have lower background due to less aggregation and larger fluorescence increase upon binding to DNA. Further testing will tell if these dyes are well suited for real-time PCR.

BEBO has been used in this study in real-time PCR and compared with SYBR Green I. A dye binding to the minor groove of dsDNA does not perturb the DNA duplex like intercalating dyes, which could be useful in for example fluorescence microscopy studies.

BEBO is an asymmetric cyanine dye and is designed with a curve shape complementary to the convex floor of the minor groove. The cyanine chromophore of BEBO is the same as that of BO. The shape is similar to other minor groove binding dyes such as Hoechst and DAPI, but BEBO shows a higher fluorescence increase when bound to DNA and absorbs at a higher, more convenient wavelength. Most minor groove binders and possibly also BEBO still intercalate in GC-rich regions, while in AT-regions it clearly binds to the minor groove. This study will analyze if and how the PCR-reaction is affected by the binding of BEBO and how it compares to the commonly used as detection reagent SYBR Green I.

MATERIALS AND METHODS

BEBO was supplied in a 5.8 mM stock solution in DMSO. Two real-time PCR instruments were used for the investigation: LightCycler from Roche and the Rotorgene from Corbett Research. A previously developed and optimized PCR-system was used, amplifying a 240 bp template from a stock of purified PCR-product. The concentrations for reagents used were [Mg]=3 mM, [dNTP]=200 μM, [primers]=0.4 μM, [BSA]=0.2 mg/ml and 1 U of Taq polymerase. 100 μM BEBO and 100X SYBR Green stock solutions were prepared in DMSO. Absorption maximum for BEBO is 467 nm and emission at 492 nm. The Rotorgene (Channel 1 Excit: 470, Detect: 510) and the LightCycler (Excit: 470, Detect Ch 1: 530) both offer appropriate detection conditions. Efficiency (E) is defined as $P_N=P_O(1+E)^n$, and is unless stated otherwise derived from a template dilution series as $E=10^{-1/a}-1$ where a is the slope of the corresponding standard curve. For further details the reader is referred to protocols and the laboratory notebook.

RESULTS OF PCR

Figure 9:
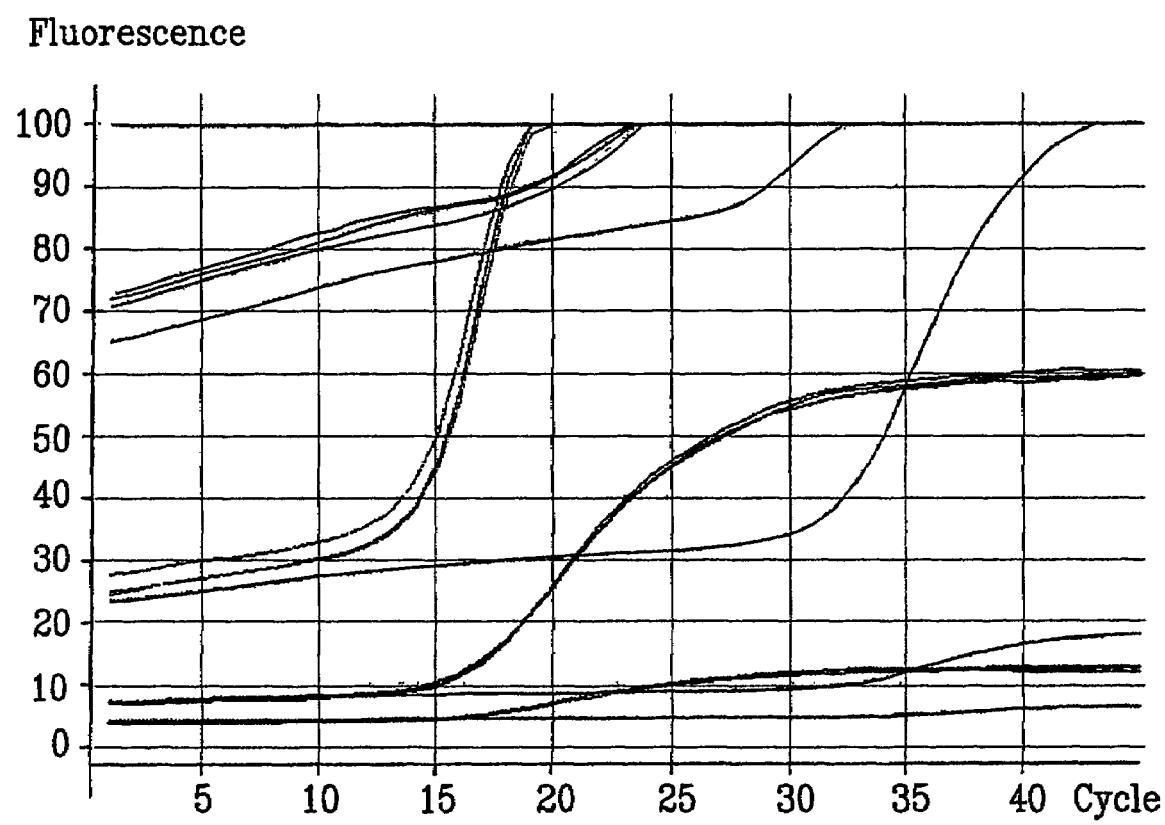
FIG. 9. BEBO dilution, raw data. Triplicates of five different concentrations of BEBO, positive and NTC. From top to bottom (left axis): 5 μM (brown), 2 μM (purple), 0.8 μM (green), 0.2 μM (blue) and 0.05 μM (red).
Figure 10:
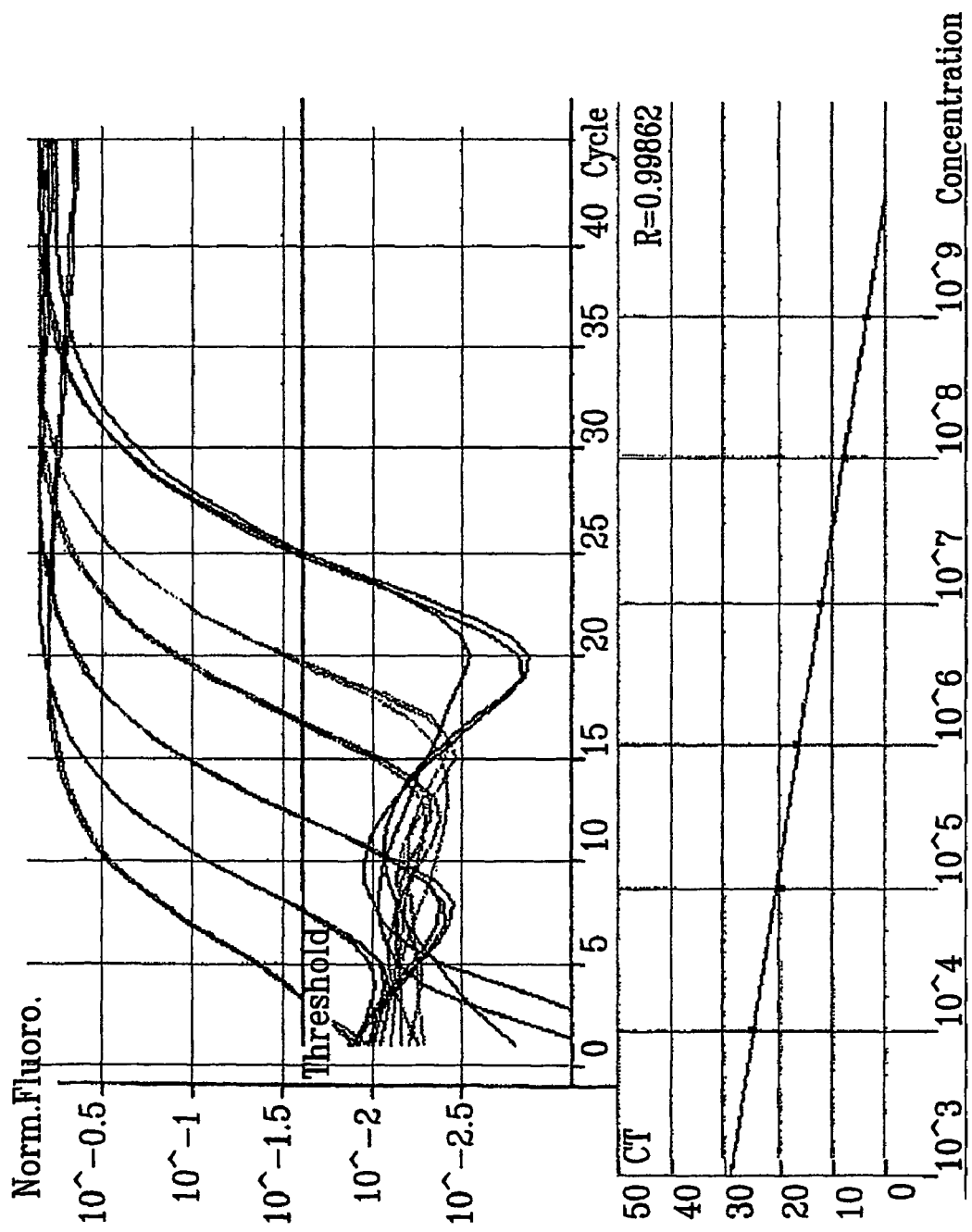
FIG. 10. Template dilution, normalized data, and the corresponding standard curve. [BEBO]=0.2 μM. Six 10-fold dilutions of purified PCR-product, from $10^9$ to $10^4$ copies/rxn. E=0.74. The fifth sample ($10^5$ copies) was shown to be incorrectly diluted and should cross the threshold approximately one cycle later.
Figure 11:
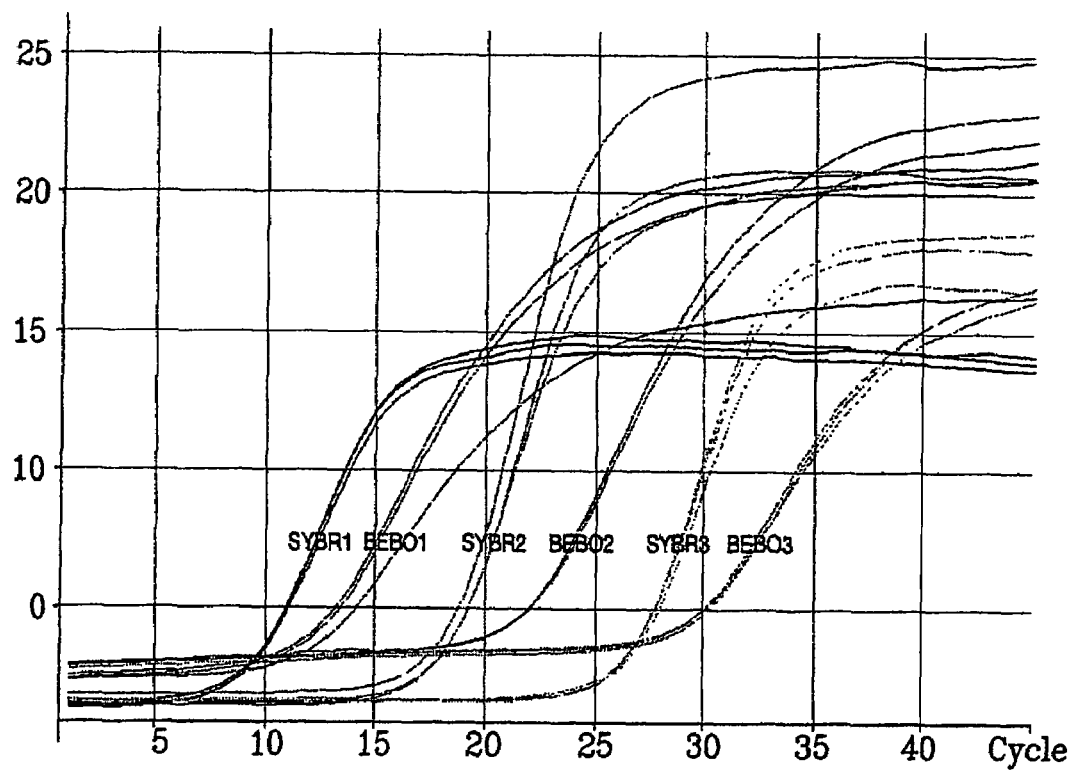
FIG. 11. BEBO vs SYBR Green, raw data. Triplicates with three 100-fold template dilutions. This figure shows the higher background fluorescence level for BEBO and the total fluorescence increase. Note the linear increase in background fluorescence for the BEBO samples.
Figure 12:
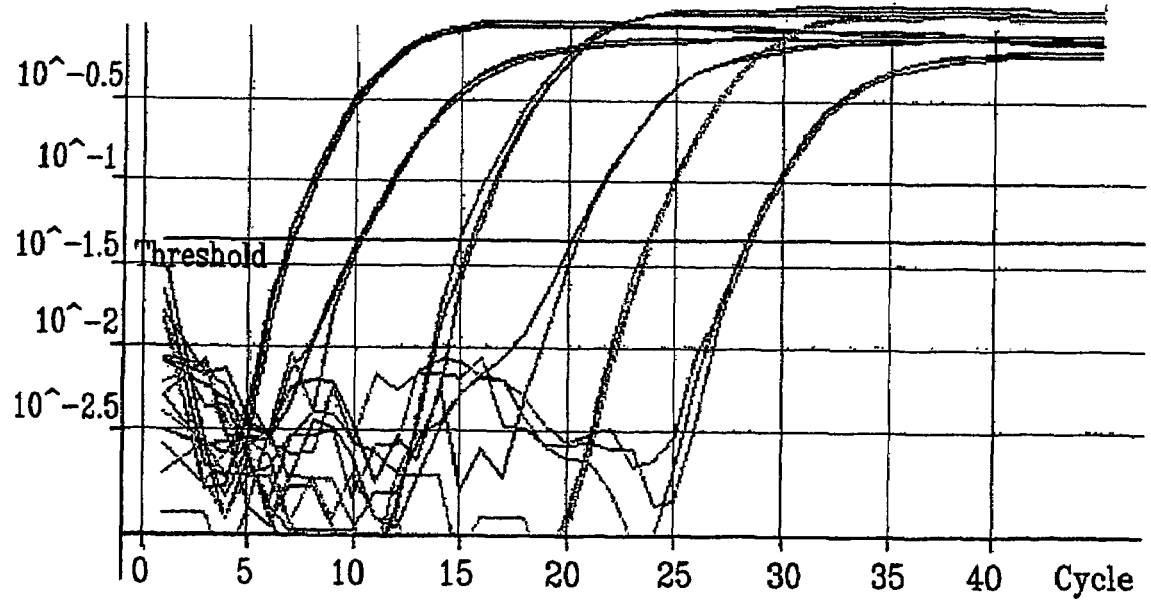
FIG. 12. BEBO vs SYBR Green, normalized data. BEBO crosses approximately four cycles later than SYBR Green for the same template concentration.
Figure 14:
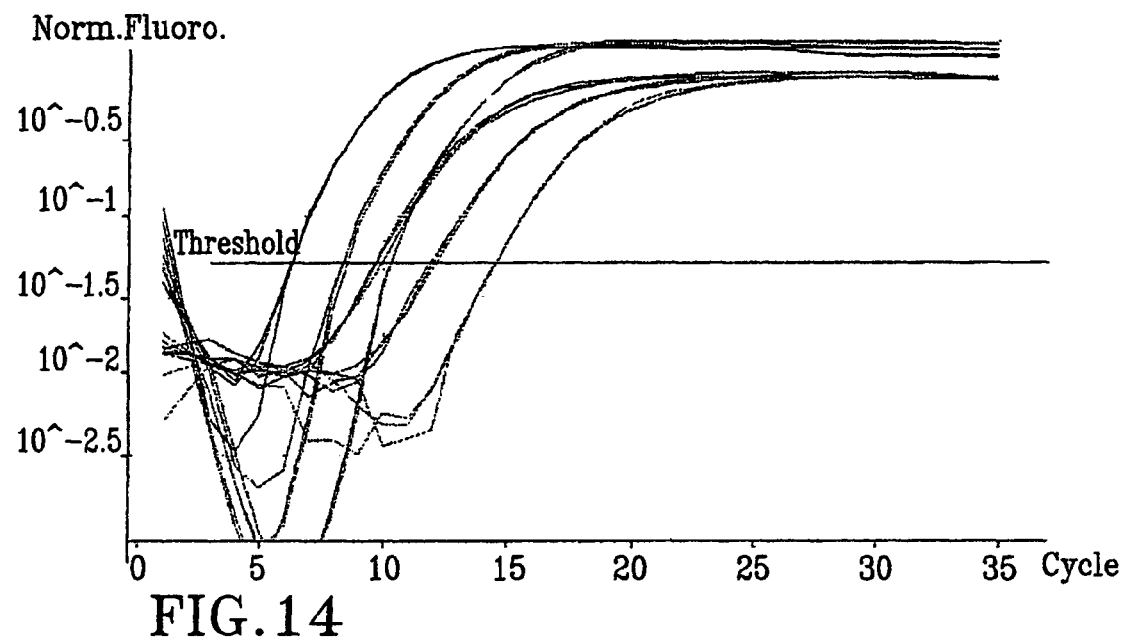
FIG. 14. BEBO vs SYBR Green. Normalized data. A 4.5-cycle shift is observed across the whole range of dilutions.
Figure 15:
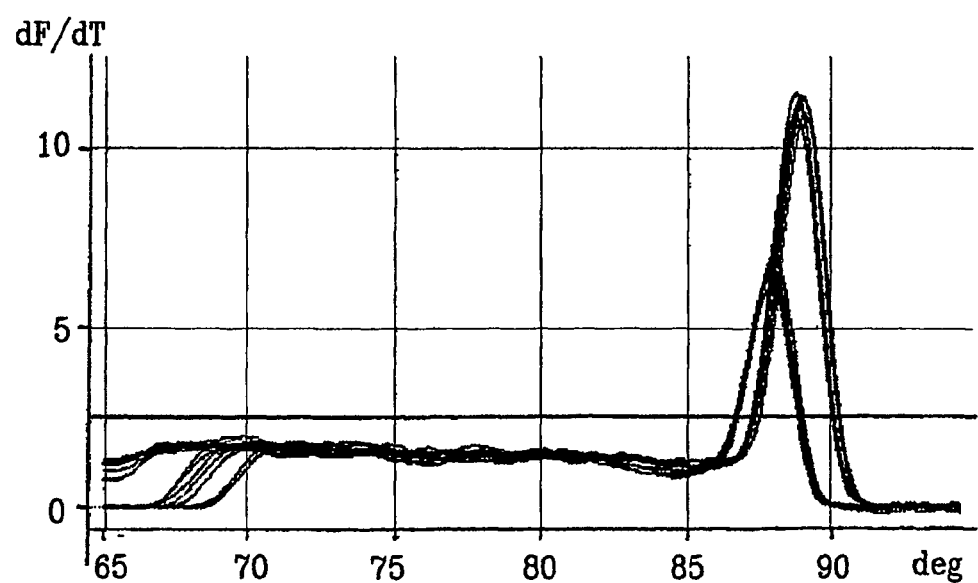
FIG. 15. Melt curve. BEBO samples have melting peak average at 87.9° C., SYBR Green samples melting peak average at 88.9° C.
Figure 16:
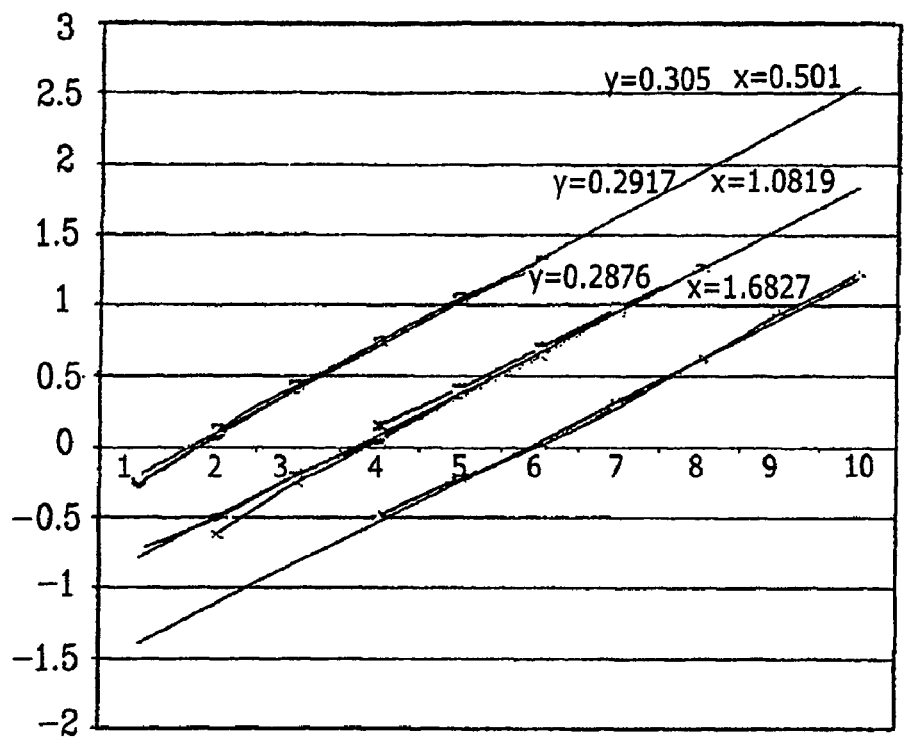
FIG. 16. Logarithmic display of a part of the exponential growth phase of SYBR Green (upper) and BEBO (lower) and its corresponding linear regression.
Figure 16:
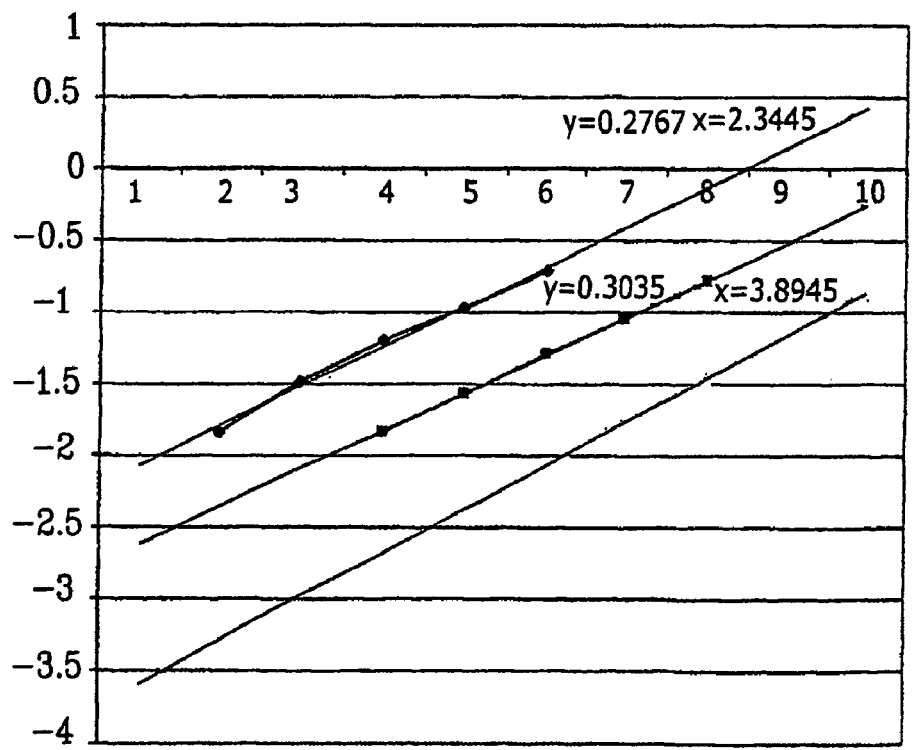
Figure 17:
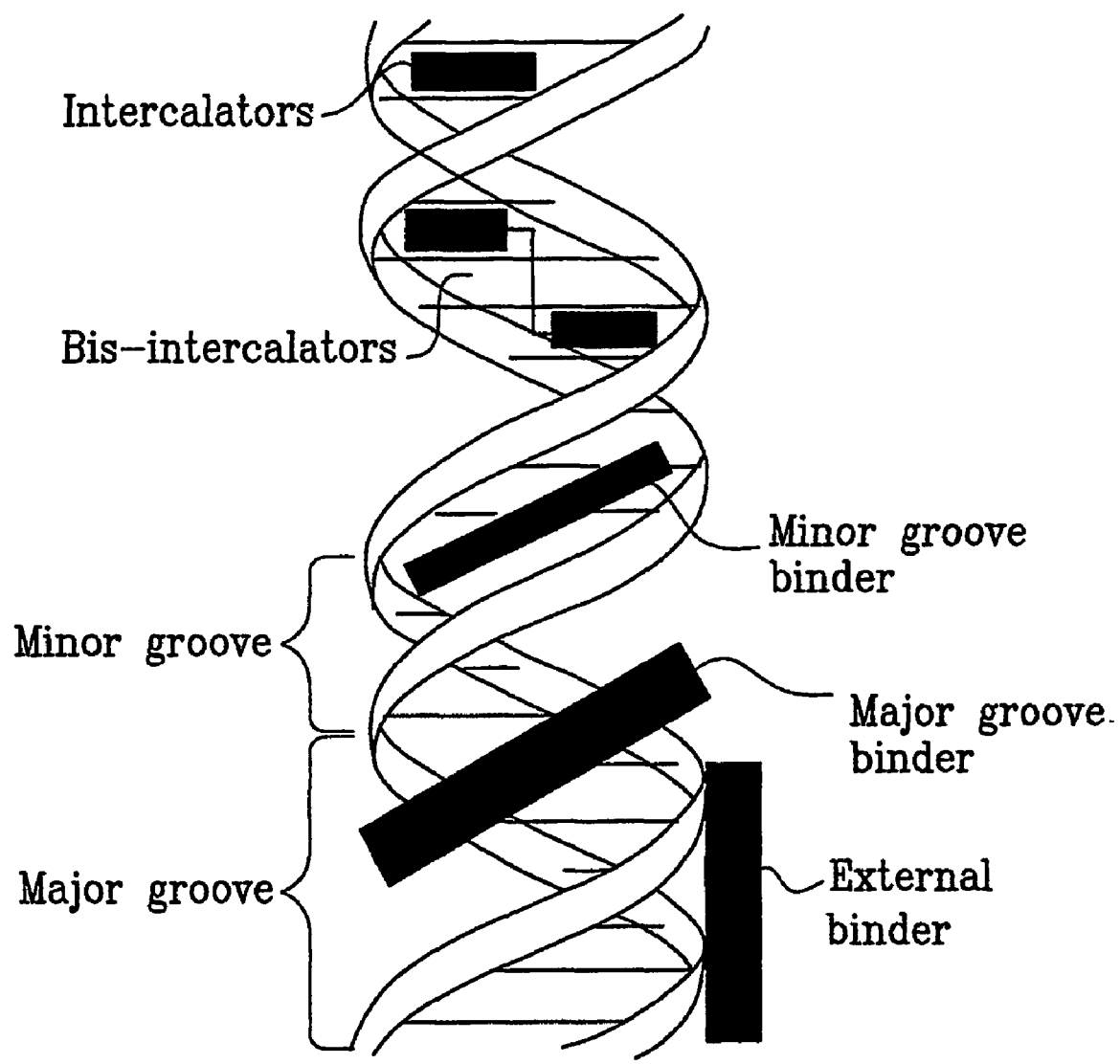
FIG. 17. Different types of DNA binding modes.

A description of attached protocols and data-files is given in Table 1. Dilution series of BEBO (0.05-5 μM) on the RotorGene (FIG. 9) indicated that 0.2 M is a good balance between background fluorescence and signal increase and this concentration was subsequently used in template dilutions and in comparison with SYBR Green. As an indication of the level of PCR inhibition, a template dilution series was performed (FIG. 10) and the efficiency was determined to be 74%. FIGS. 11-12 show a comparison with SYBR Green (0.1X) and the results indicate that BEBO has higher fluorescence background and lower fluorescence increase. Efficiencies calculated from the dilutions were 66% for BEBO and 72% for SYBR Green. This is lower than usually observed for this PCR-system using SYBR Green. BEBO-samples are consistently seen approximately 4 cycles later than the SYBR Green equivalent. To test whether DMSO could decrease the high background fluorescence, 15% DMSO was present in six samples (data not shown). Although DMSO in concentrations of up to 20% is commonly used to increase specificity in PCR, total inhibition was observed. A second comparison between BEBO and SYBR Green was performed with minor modifications to the protocol (FIG. 14), [BEBO]=0.4 μM, [SYBR Green]=0.2X, giving 80% and 99% efficiency respectively.

This study indicates that BEBO is an appropriate non-specific dsDNA-binding dye for use in real-time PCR. The concentration range of optical use for real-time PCR in the instruments used is 0.1-0.5 μM. Higher concentrations result in high unwanted background fluorescence while lower concentration than 0.05 μM does not give enough fluorescence increase.

BEBO does not give rise to large inhibition of the polymerase chain reaction in the lower range of the concentration interval mentioned above. A major disturbance of the reaction occurs at concentrations above 1 μM, where the PCR loses its specificity and only forms short, unspecific products, most likely primer dimers. Inhibition is observed at 0.4 μM, while 0.2 μM BEBO doesn't seem to inhibit the PCR to any great extent.

When comparing BEBO with SYBR Green the most striking differences are the increased background fluorescence and the delay in Ct at the same template concentration. The efficiencies are higher for SYBR Green: 72% vs 66% for [SYBR]=0.1X and [BEBO]=0.2 μM, and 99% vs 80% for [SYBR]=0.2X and [BEBO]=0.4 μM. The final fluorescence reached is similar, while the background of BEBO is approximately twice that of SYBR Green.

Figure 13:
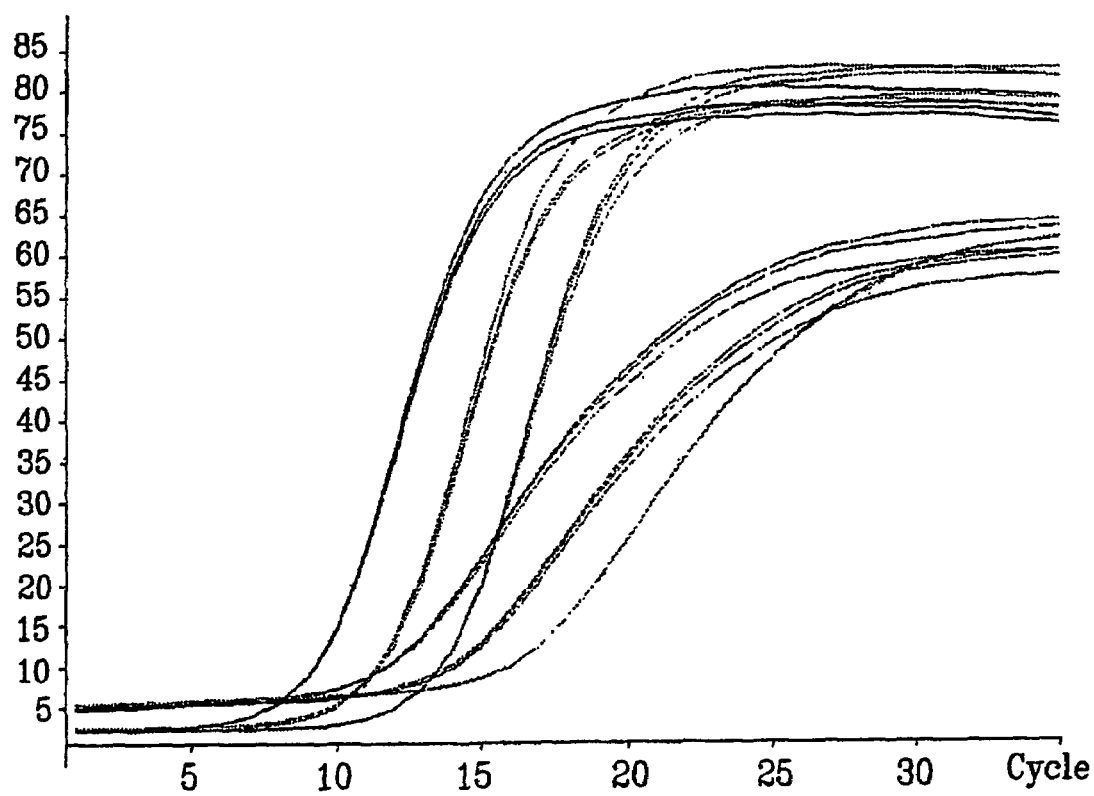
FIG. 13. BEBO vs SYBR Green, raw data, triplicate 4-fold dilutions. [BEBO]=0.4 μM, [SYBR]=0.2X. The linear increase in background fluorescence is seen for BEBO but not for SYBR Green.

The background fluorescence is caused by aggregation of BEBO, resulting in spontaneous fluorescence. This aggregation seems to accumulate as the PCR is running, indicated by a linear increase in background signal seen in FIGS. 9, 11 and 13. At high dye concentrations, this phenomenon is also seen with SYBR Green (data not shown). To decrease the aggregation, which is virtually non-existent in ethanol or methanol, 15% DMSO was added to the reaction. The background decreased significantly, but also resulted in loss of specificity in the PCR.

When using the LightCycler it was observed that much higher probe concentrations were needed to reach inhibition of the PCR. Up to 5 μM BEBO gave specific product using the LightCycler while 2 μM BEBO on the RotorGene gave no product. We conclude that this is due to significant adsorption to the glass surface of the glass capillaries used in the LightCycler instrument.

Presently, the information about structure, binding mode, molar concentration, etc. of SYBR Green I is very scarce. This makes a detailed comparison with BEBO difficult and some applications may require information about the dye used, currently only available for BEBO.

CURVE ANALYSIS

Figure 8:
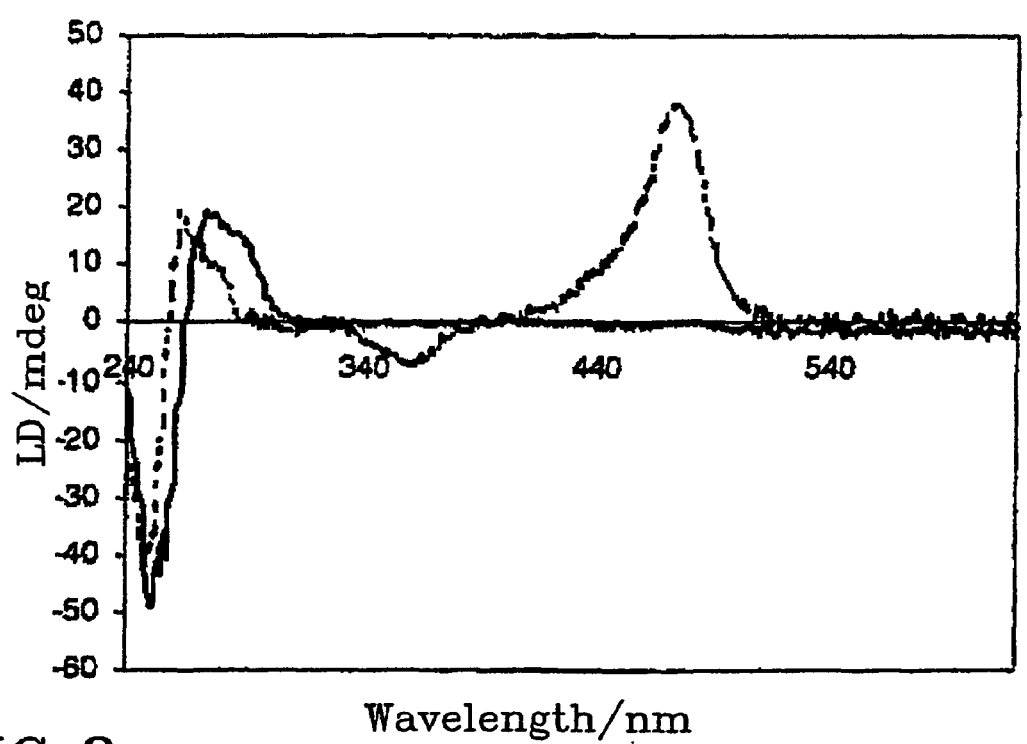
FIG. 8. CD spectra of BEBO complexed with: ( - - - ) poly[dA-dT]$_2$, ( - - - ) poly [dG-dC]$_2$, at R=0.05 and R=0.02, respectively.

To further analyze the amplification curves, regression of the exponential growth phase was calculated (FIG. 8). The analysis was focused on the data from the second comparison between BEBO and SYBR Green. BEBO had an average efficiency of 0.91 and SYBR Green 0.97. This compares with the efficiency calculated from the dilution series: 0.80 and 0.99 respectively.

The reason for BEBO to reach threshold approximately 4 cycles later than SYBR Green at the same template concentration is probably the lower fluorescence increase upon binding to dsDNA. Lower efficiency alone cannot explain the whole delay of 4 cycles, and this is confirmed by the efficiency derived from the curve analysis. SYBR Green binds effectively to the DNA during PCR and shows an early fluorescence effect. However, this effect seems to be too strong, as the PCR reaction is delayed during multiplication using SYBR Green, which is a disadvantage. Thus the SYBR Green interferes with the DNA molecule to an extent that may not be desirable.

REFERENCES

1. Rye, H. S.; Yue, S.; Wemmer, D. E.; Quesada, M. A.; Haugland, R. P.; Mathies, R. A.; Glazer, A. N. *Nucleic Acids Res.* 1992, 11, 2803-2812.
2. Lee, L. G.; Chen, C.-H.; Chiu, L. A. *Cytometry* 1986, 7, 508-517.
3. Svanvik, N.; Westman, G.; Wang, D.; Kubista, M. *Anal. Biochem.* 2000, 281, 26-35.
4. Gurrieri, S.; Wells, K. S.; Johnson, I. D.; Bustamante, C. *Anal. Biochem.* 1997, 249, 44-53.
5. Netzel, T. L.; Nafisi, K.; Zhao, M.; Lenhard, J. R.; Johnson, I. *J. Phys. Chem.* 1995, 99, 17936-17947.
6. Larsson, A.; Carlsson, C.; Jonsson, M.; Albinsson, B. *J. Am. Chem. Soc.* 1994, 116, 8459-8465.
7. Larsson, A.; Carlsson, C.; Jonsson, M. *Biopolymers* 1995, 36, 153-167.
8. Petty J. T.; Bordelon, J. A.; Robertson, M. E. *J. Phys. Chem. B* 2000, 104, 7221-7227.
9. Nygren, J.; Svanvik, N.; Kubista, M. *Biopolymers* 1998, 46, 39-51.
10. Kapuscinski, J.; Skoczylas, B. *Nucleic Acids Res.* 1978, 5, 3775-3799.
11. Jorgenson, K. F.; Varshney, U.; van de Sande, J. H. *J. Biomol. Struct. Dyn.* 1988, 5, 1005-1023.
12. Neidle, S. *Biopolymers* 1997, 44, 105-121.
13. Yoshinaga, N.; Akitaya, T.; Yoshikawa, K. *Biochem. Biophys. Res. Comm.* 2001, 286, 264-267.
14. Matsuzawa, Y.; Yoshikawa, K. *Nucleosid. Nucleotid.* 1994, 13, 1415-1423.
15. Isacsson, J.; Westman, G. *Tetrahedron Lett.* 2001, 42, 3207-3210.
16. Singer, V. L.; Jones, L. J.; Yue, S. T.; Haugland, R. P. *Anal. Biochem.* 1997, 249, 228-238.
17. Haugland, R. P. *Handbook of Fluorescent Probes and Research Chemicals, 6th Edition,* 1996, 144-152.
18. Mikheikin, A. L.; Zhuze, A. L.; Zasedatelev, A. S. *J. Biomol. Struct. Dyn.* 2000, 18, 59-72.
19. Seifert, J. L.; Connor, R. E.; Kushon, S. A.; Wang, M.; Armitage, B. A. *J. Am. Chem. Soc* 1999, 121, 2987-2995.
20. Deligeorgiev, T. G.; Gadjev, N. I.; Drexhage, K.-H.; Sabnis, R. W. *Dyes and Pigments* 1995, 29, 315-322.
21. Mital, R. L.; Jain, S. K. *J. Chem. Soc. C* 1969, 2148-2150.
22. Naim, S. S.; Singh, S. K.; Sharma, S. *Ind. J. Chem.* 1991, 30B, 494-498.
23. Zhou, X. F.; Peng, Z. H.; Geise, H. J.; Peng, B. X.; Li, Z. X.; Yan, M.; Dommisse, R.; Carleer, R.; Claeys, M. *J. Imaging Sci. Technol.* 1995, 39, 244-252.
24. Nordén, B.; Kubista, M.; Kurucsev, T. *Quart. Rev. Biophys.* 1992, 25, 51-170.
25. Kubista, M.; Åkerman, B.; Nordén, B. *Biochemistry* 1987, 26, 4545-4553.
26. Carlsson, C.; Larsson, A.; Jonsson, M.; Albinsson, B.; Nordén, B. *J. Phys. Chem.* 1994, 98, 10313-10321.
27. Wilson, W. D.; Tanious, F. A.; Barton, H. J.; Strekowski, L.; Boykin, D. W.; Jones, R. L. *J. Am. Chem. Soc.* 1989, 111, 5008-5010.
28. Colson, P.; Bailly, C.; Houssier, C. *Biophys. Chem.* 1996, 58, 125-140.
28. Lyng, R.; Rodger, A.; Nordén, B. *Biopolymers* 1992, 32, 1201-1214.
30. Ogul'chansky, T. Y.; Losytskyy, M. Y.; Kovalska, V. B.; Yashchuk, V. M.; Yarmoluk, S. M. *Spectrochim. Acta A* 2001, 57, 1525-1532.

The invention claimed is:

1. A cyanine dye having the formula:

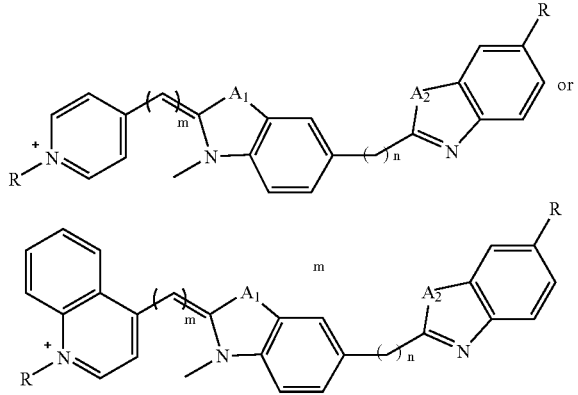

wherein $A_1$ and $A_2$ are each independently O, S or N, and R is H or a hydrocarbon, optionally containing a heteroatom, and m is an integer from 0 to 5, and n is an integer from 0 to 5.

2. The cyanine dye of claim 1, wherein R is methyl or ethyl, and m is 1 and n is 0.

3. The cyanine dye of claim 1, wherein R is methyl or ethyl, m is 1 and n is 0, and $A_1$ and $A_2$ are S.

4. The cyanine dye of claim 1, wherein R is methyl or ethyl, m is 1 and n is 0, and $A_1$ and $A_2$ are O.

5. The cyanine dye of claim 1, wherein R is methyl or ethyl, m is 1 and n is 0, $A_1$ is S and $A_2$ is O.

6. A hybridization probe comprising a sequence-recognizing nucleic acid portion and a reporter portion, wherein the reporter portion comprises a cyanine dye having the formula:

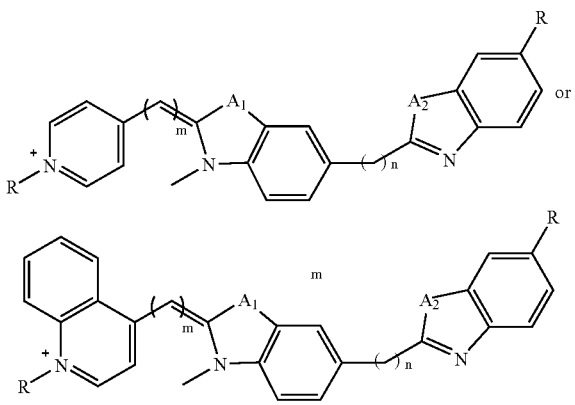

wherein $A_1$ and $A_2$ are each independently O, S or N, and R is H or a hydrocarbon, optionally containing a heteroatom, and m is an integer from 0 to 5, and n is an integer from 0 to 5.

7. The probe of claim 6, wherein R is methyl or ethyl, and m is 1 and n is 0.

8. The probe of claim 6, wherein R is methyl or ethyl, m is 1 and n is 0, and $A_1$ and $A_2$ are S.

9. The probe of claim 6, wherein R is methyl or ethyl, m is 1 and n is 0, and $A_1$ and $A_2$ are O.

10. The probe of claim 6, wherein R is methyl or ethyl, m is 1 and n is 0, $A_1$ is S and $A_2$ is O.

11. A method for detecting the presence of double-stranded DNA in a sample comprising the steps of: introducing into the sample a cyanine dye having the formula:

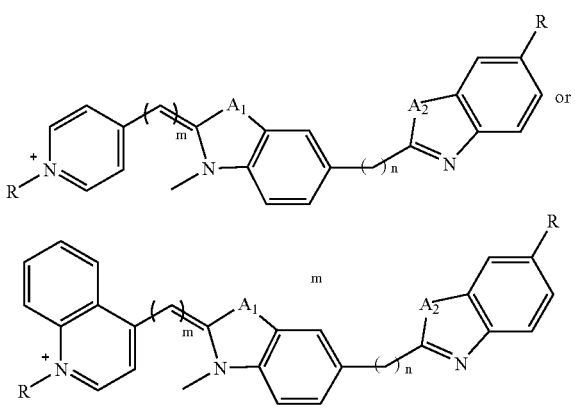

wherein $A_1$ and $A_2$ are each independently O, S or N, and R is H or a hydrocarbon, optionally containing a heteroatom, and m is an integer from 0 to 5, and n is an integer from 0 to 5; and detecting fluorescence from the cyanine dye, wherein the fluorescence intensity from the cyanine dye is increased in the presence of double-stranded DNA as a result of binding of the cyanine dye in the minor groove of the double-stranded DNA.

12. The method of claim 11, wherein R is methyl or ethyl, and m is 1 and n is 0.

13. The method of claim 11, wherein R is methyl or ethyl, m is 1 and n is 0, and $A_1$ and $A_2$ are S.

14. The method of claim 11, wherein R is methyl or ethyl, m is 1 and n is 0, and $A_1$ and $A_2$ are O.

15. The method of claim 11, wherein R is methyl or ethyl, m is 1 and n is 0, $A_1$ is S and $A_2$ is O.

16. A method for monitoring a real time PCR reaction by detection of the formation of double-stranded DNA, comprising the steps of performing real time PCR in the presence of a fluorescent dye that interacts with double-stranded DNA, and monitoring fluorescence from the fluorescent dye, wherein the fluorescent dye increases its fluorescent intensity when it is locked in a minor groove position in double stranded DNA, and wherein the dye comprises a cyanine dye having the formula:

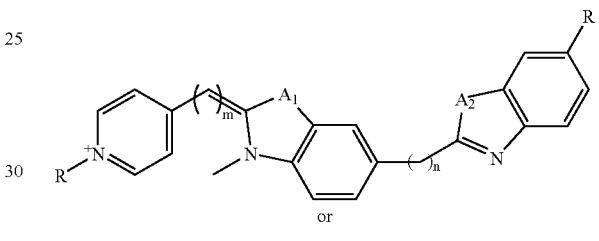

or

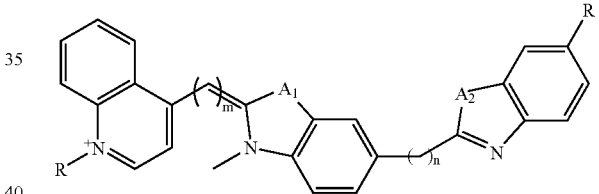

wherein $A_1$ and $A_2$ are each independently O, S or N, and R is H or a hydrocarbon, optionally containing a heteroatom, and m is an integer from 0 to 5, and n to an integer from 0 to 5.

17. The method of claim 16, wherein R is methyl or ethyl, and m is 1 and n is 0.

18. The method of claim 16, wherein R is methyl or ethyl, m is 1 and n is 0, and $A_1$ and $A_2$ are S.

19. The method of claim 16, wherein R is methyl or ethyl, m is 1 and n is 0, and $A_1$ and $A_2$ are O.

20. The method of claim 16, wherein R is methyl or ethyl, m is 1 and n is 0, $A_1$ is S and $A_2$ is O.

* * * * *